(12) United States Patent
Fyfe et al.

(10) Patent No.: US 10,213,158 B2
(45) Date of Patent: Feb. 26, 2019

(54) SYSTEMS AND METHODS FOR BIOMETRIC SENSING WITH SENSOR FUSION

(71) Applicant: 4iiii Innovations Inc., Cochrane (CA)

(72) Inventors: Kipling Fyfe, Cochrane (CA); Tom Williams, Edmonton (CA); Darren Zacher, Calgary (CA)

(73) Assignee: 4iiii Innovations Inc., Cochrane, Alberta (CA)

( * ) Notice: Subject to any disclaimer, the term of this patent is extended or adjusted under 35 U.S.C. 154(b) by 78 days.

(21) Appl. No.: 15/108,376

(22) PCT Filed: Jan. 6, 2015

(86) PCT No.: PCT/IB2015/000358
§ 371 (c)(1),
(2) Date: Jun. 27, 2016

(87) PCT Pub. No.: WO2015/101947
PCT Pub. Date: Jul. 9, 2015

(65) Prior Publication Data
US 2016/0317089 A1    Nov. 3, 2016

Related U.S. Application Data

(60) Provisional application No. 61/924,079, filed on Jan. 6, 2014.

(51) Int. Cl.
*A61B 5/00* (2006.01)
*A61B 5/024* (2006.01)
(Continued)

(52) U.S. Cl.
CPC .......... *A61B 5/6813* (2013.01); *A61B 5/0002* (2013.01); *A61B 5/0008* (2013.01);
(Continued)

(58) Field of Classification Search
USPC .................................................. 600/300–301
See application file for complete search history.

(56) References Cited

U.S. PATENT DOCUMENTS

2008/0211766 A1*  9/2008  Westerman ............. G06F 3/038
345/156

FOREIGN PATENT DOCUMENTS

| CN | 101785659 A | 7/2010 |
| WO | 98/17172 A2 | 4/1998 |
| WO | 200885759 A2 | 7/2008 |

OTHER PUBLICATIONS

Großhauser, T., et al.; Wearable Multi-Modal Sensor System for Embedded Audio-Haptic Feedback; Proceedings of ISon 2010, 3rd Interactive Sonification Workshop, KTH, Stockholm, Sweden, Apr. 7, 2010, pp. 75-79.
(Continued)

*Primary Examiner* — Nicole F Lavert
(74) *Attorney, Agent, or Firm* — Lathrop Gage LLP

(57) ABSTRACT

A system and method implement biometric sensing with sensor fusion. A first sensor is coupled with a user and is capable of sensing a first characteristic of the user. A second sensor is coupled with the user and is capable of sensing a second characteristic of the user. A memory stores software with machine readable instructions that when executed by a processor implement an algorithm to correct for motion artifacts included within the second characteristic based upon activity of the user determined from the first characteristic.

6 Claims, 17 Drawing Sheets

(51) Int. Cl.
  *A61B 5/053*   (2006.01)
  *A61B 5/11*   (2006.01)
  *A61B 5/0205*   (2006.01)
  *A61B 5/08*   (2006.01)
  *A61B 5/145*   (2006.01)
  *A61B 5/1455*   (2006.01)
  *A61B 5/01*   (2006.01)

(52) U.S. Cl.
  CPC ...... *A61B 5/02055* (2013.01); *A61B 5/02416* (2013.01); *A61B 5/0533* (2013.01); *A61B 5/0809* (2013.01); *A61B 5/1112* (2013.01); *A61B 5/1118* (2013.01); *A61B 5/14532* (2013.01); *A61B 5/14546* (2013.01); *A61B 5/14551* (2013.01); *A61B 5/4875* (2013.01); *A61B 5/6801* (2013.01); *A61B 5/6802* (2013.01); *A61B 5/721* (2013.01); *A61B 5/7207* (2013.01); *A61B 5/7275* (2013.01); *A61B 5/7282* (2013.01); *A61B 5/7455* (2013.01); *A61B 5/0022* (2013.01); *A61B 5/01* (2013.01); *A61B 5/024* (2013.01); *A61B 5/0816* (2013.01); *A61B 5/1117* (2013.01); *A61B 5/681* (2013.01); *A61B 5/6804* (2013.01); *A61B 5/6831* (2013.01); *A61B 5/6838* (2013.01); *A61B 5/7405* (2013.01); *A61B 2503/10* (2013.01); *A61B 2560/0223* (2013.01)

(56) References Cited

OTHER PUBLICATIONS

PCT/IB2015/000358 International Search Report & Written Opinion dated Jul. 10, 2015, 8 pages.

\* cited by examiner

SNAP-ON WITH KNOBBY POST / CAVITY

RING SEGMENT SECURING TO A GROOVE OR INDENTATION AROUND THE POD

PLIABLE LOOP SECURING TO A GROOVE OR INDENTATION AROUND THE POD

SINGLE PIECE - BELT CLIP MOLDED IN RIGID PLASTIC

OPTIONAL: SOFT RUBBER OVERMOLDED TO ADD GRIP

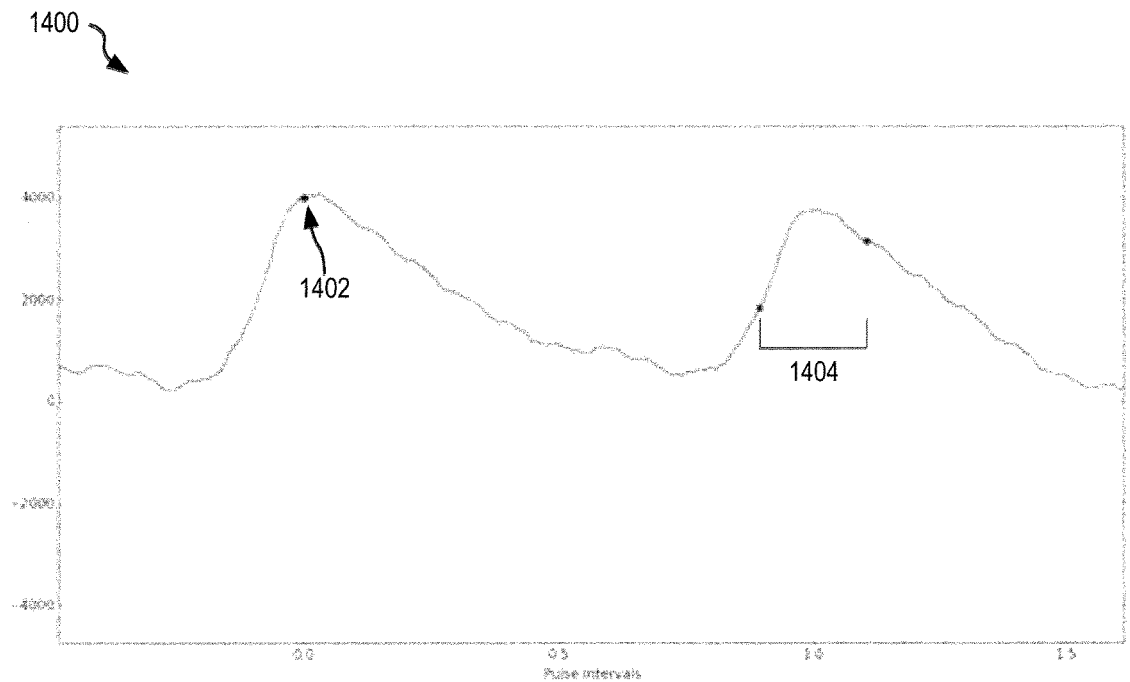

FIG. 14

| Biofeedback Source | LED light | Audio | Vibration | Point heat source | Electric shock |
|---|---|---|---|---|---|
| Customizations | Colour | Pitch | Buzz rate | Temperature | Voltage |
| | Intensity | Volume | Buzz intensity | Surface area / number of points | Current |
| | On time | On time | On time | | On time |
| | Off time | Off time | Off time | | Off time |
| | Sequence or pattern of the above | Sequence or pattern of the above | Sequence or pattern of the above | | Sequence or pattern of the above |

| Notification Source | Filter Criteria |
|---|---|
| Phone call | From specified person(s) |
| Email | Containing specific keywords, from specific addresses, etc. |
| SMS or Social Media Message | From specified person(s) |
| Tweet | From specified person(s), containing specific keywords, etc. |
| Social Media Notification | From specified person(s), containing specific keywords, etc. |
| | |
| | |

*FIG. 16*

SYSTEMS AND METHODS FOR BIOMETRIC SENSING WITH SENSOR FUSION

RELATED APPLICATIONS

This application claims priority to U.S. Patent Application Ser. No. 61/924,079, filed Jan. 6, 2014, and incorporated herein by reference.

BACKGROUND

Sensors may be used to measure biometrics of a user. Biometric results are determined from one or more sensors attached to the user and displayed to the user. Accuracy of these biometric results may vary as the activity of the user varies, since certain activities induce inaccuracies in sensor measurements.

SUMMARY OF THE INVENTION

In one embodiment, a system implements biometric sensing with sensor fusion. The system includes a first sensor for coupling with a user and being capable of sensing a first characteristic of the user. The system includes a second sensor for coupling with the user and being capable of sensing a second characteristic of the user. The system includes a processor and memory storing software with machine readable instructions that when executed by the processor implement an algorithm to correct for motion artifacts included within the second characteristic based upon activity of the user determined from the first characteristic.

In another embodiment, a method implements biometric sensing with sensor fusion. Within a first pod positioned at a first location of a user's body, a first characteristic of the user is detected. The first pod receives a wireless signal indicative of a second characteristic of the user from a second pod positioned at a second location of the user's body. An activity of the user is determined based upon the first and second characteristics.

BRIEF DESCRIPTION OF THE FIGURES

FIG. 14 is a graph illustrating an identified first peak within sensor data from the sensor of the sensor pod of FIG. 1, in an embodiment.

FIG. 15 shows one exemplary table illustrating exemplary customizations of biofeedback sources with the sensor pod of FIG. 1.

FIG. 16 shows a table defining exemplary notification sources and filter criteria that may be configured with one or both of the mobile device and the sensor pod of FIG. 1.

DETAILED DESCRIPTION OF THE EMBODIMENTS

Definitions

Figure 1A:
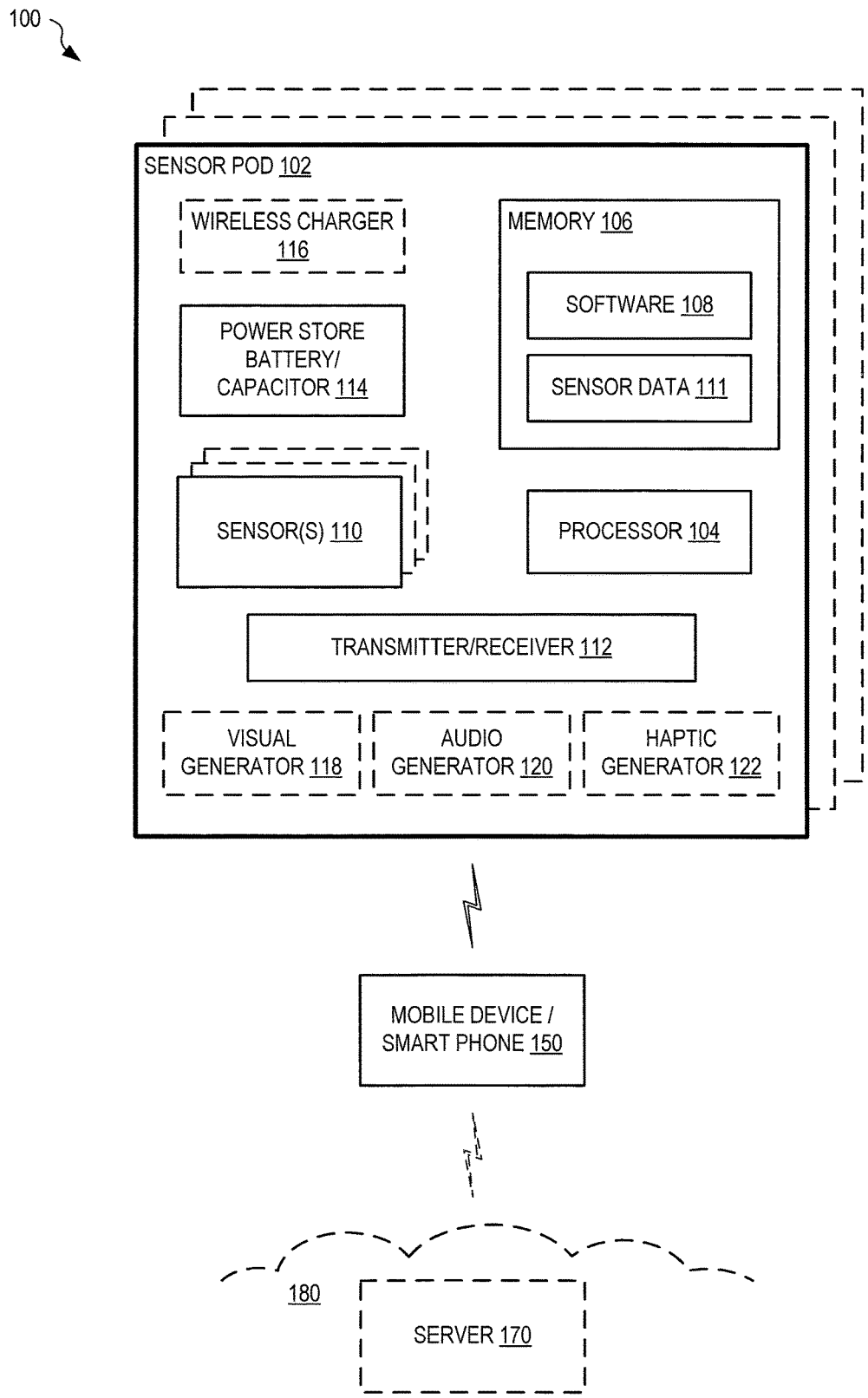
FIG. 1A shows one exemplary system for biometric sensing with sensor fusion, in an embodiment.

Photoplethysmogram—A photoplethysmogram (PPG) is an optically obtained plethysmogram, a volumetric measurement of an organ. A PPG is often obtained by using a pulse oximeter that illuminates the skin and measures changes in light absorption. A conventional pulse oximeter monitors the perfusion of blood to the dermis and subcutaneous tissue of the skin. The change in volume caused by the pressure pulse is detected by illuminating the skin with the light from a light-emitting diode (LED) and then measuring the amount of light either transmitted or reflected to a photodiode. (source: Wikipedia)

Fabrication Material—A material that can be used to fabricate device or an attachment point, e.g. fabric, metal, rubber, plastic, resin, silicon, or composite, etc.

Against the Skin—Being located touching the skin or separated by only a thin layer made of fabrication material.

Measurement Site Reliability Factor—An empirically determined factor used to adjust the weighting of a sensor measurement from a given site on the body.

Method of Attachment

A method of attaching the pod to a wearable piece of clothing, accessory or attachment point including: (a) Snap-On with knobby post/cavity, (b) ring segment securing to a groove or indentation around the pod, (c) pliable loop securing to a groove or indentation around the pod, (d) magnetics, (e) post through one or more holes in the pod, with the holes being along any axis, (f) form-fitting overmold, (g) tension strap pressed into a cavity on the surface of the pod, (h) key hole/key chain, and (i) pocket.

Overview

The invention describes three types of embodiments. In a first embodiment, a plurality of acoustic, electromagnetic, and/or pressure based (e.g. ultrasonic, laser, PPG, RF, and ECG) heart rate and other biofeedback sensors (e.g., motion, respiration, temperature, galvanic skin response) cooperate to make useful determinations of body state (heart rate, motion, temperature, respiration, and other biofeedback measurements) through a fusion of sensors with wireless communication. One or more sensors and accompanying electronics may be contained in a discrete pod that is integrated into clothing or designed with an attachment point. In a second embodiment, a plurality of acoustic, electromagnetic, and/or pressure based (e.g. ultrasonic, laser, PPG, RF, and ECG) heart rate and other biofeedback sensors (e.g., motion, respiration, temperature, galvanic skin response) make useful determinations of body state (heart rate, motion, temperature, respiration, and other biofeedback measurements) through a fusion of sensors, with biofeedback notification (haptic, audible, light, temperature, electrical, etc.), and optionally wireless communication, in a discrete pod that is integrated into clothing or configured with an attachment point. In a third embodiment, a plurality of biofeedback notification (haptic, audible, light, temperature, electrical, etc.) actuators and wireless communications are configured in a discrete pod that is integrated into clothing or configured with an attachment point. For example, one or more sensor pods may be: (i) clipped onto undergarments, (ii) secured to the underside of a wrist watch, (iii) held in place by the tension of an elastic fabric swimsuit or wetsuit, and (iv) used as a strap or band around a part of the body (wrist, ankle, trunk, neck, head).

FIG. 1A shows one exemplary system 100 for biometric sensing with sensor fusion. A sensor pod 102 includes one or more of a processor 104, a memory 106, software 108 stored within memory 106, at least one sensor 110, a transmitter/receiver 112, and a power store 114. Optionally, sensor pod 102 includes a wireless charger 116 for charging power store 114 wirelessly, a visual generator 118 (e.g., LEDs), an audio generator 120 (e.g., a speaker), and a haptic generator 122 (e.g., a vibrator). Memory 106 may be implemented as one or more of RAM, ROM, FLASH, magnetic, and optical data storage. In an embodiment, processor 104 and memory 106 are implemented together as a microcontroller that includes at least one interface for communicating with sensor 110.

In an embodiment, sensor pod 102 communicates wirelessly, using transmitter/receiver 112, with a mobile device 150 (e.g., a smart phone or similar device), and may thereby communicate with one or more servers 170 located within cloud 180.

Device Configurations

Figure 18:
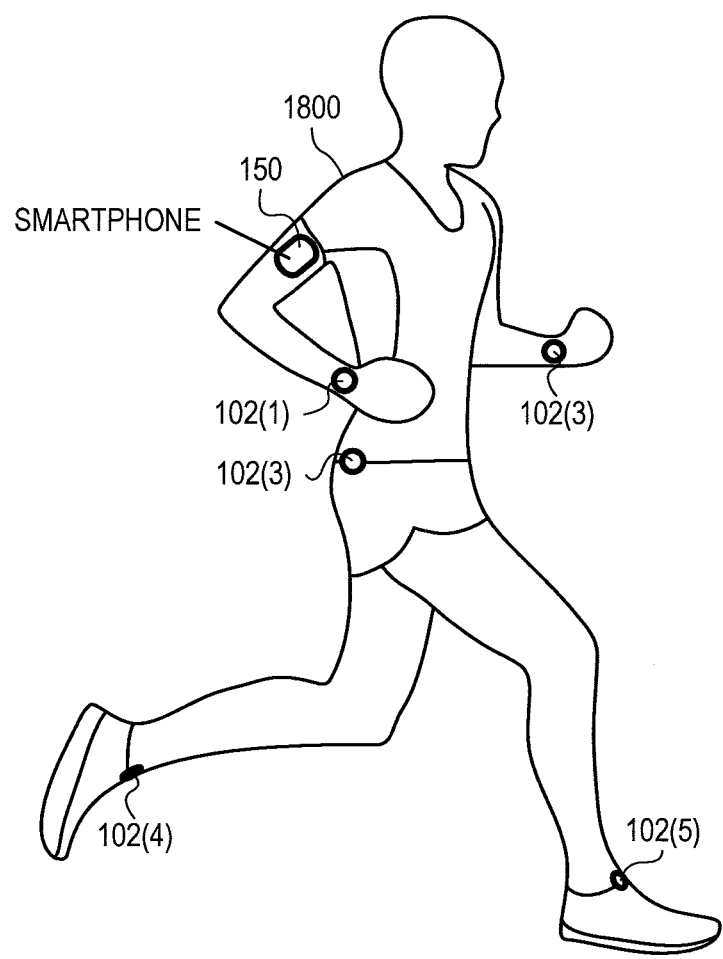
FIG. 18 shows the sensor pods of FIG. 1 positioned on a runner and communicating with the mobile device positioned on the runner's arm, in an embodiment.

Sensor pod 102 may be used in a number of different configurations, with or without being positioned against a user's skin. FIG. 18 shows sensor pods 102(1)-(5) positioned on a runner 1800, where pods 102 communicate with mobile device 150 (e.g., a smartphone) positioned on the runner's arm. Pods 102 may be placed at different locations on a user's body depending on the intended activity of the user. In the example of FIG. 18, pods 102(4) and 102(5) are positioned on feet (or ankles) of runner 1800, pods 102(1) and 102(2) are positioned on wrists of runner 1800, and pod 102(3) is positioned on the runner's waist. Pods 102 are positioned to capture movement of the user (e.g., runner 1800). For a cyclist, pods 102 may be positioned on feet or ankles of the cyclist to capture the predominant movement made by the cyclist. For a swimmer, pods 102 may be positioned on the swimmer's wrist(s) and/or ankles/feet to better capture the dominant motion of the activity. Pods 102 need not be attached to all predominant points of motion; pod 102 may be attached to one wrist of a swimmer, since motion of the other wrist may be assumed similar. Likewise, pod 102 may be attached to one ankle where movement of the other ankle may be assumed similar. Each pod 102 may be configured with sensors 110 based upon the intended position of the pod on the user's body, and thus different pods 102 may have different sensors 110.

In the exemplary configuration of FIG. 1A, one sensor pod 102 is used together with mobile device 150. Sensor pod 102 determines and sends sensor data 111 (illustratively shown stored within memory 106) to mobile device 150 and mobile device 150 provides notification data to sensor pod 102.

In the exemplary configuration of FIG. 18, the plurality of sensor pods 102 are used together, where one or more of the sensor pods 102 provides sensor data 111 to other of the sensor pods 102 and/or to mobile device 150 to collectively provide biofeedback notification(s) to runner 1800.

In a third exemplary configuration, two sensor pods 102 are used together. Each sensor pod 102 shares sensor data 111 with the other sensor pod 102 and integrates answers, derived from sensor data 111, to provide better accuracy and/or robustness.

In a fourth exemplary configuration, sensor pod 102 and a GPS source are used together. The GPS source provides location data to the user and sensor pod 102 provides other information to the user.

In a fifth exemplary configuration, sensor pod 102 is used with a watch that has one or more sensors. Sensor pod 102 sends sensor data 111 to the watch, which uses the received sensor data together with sensor data collected from its own sensors to improve accuracy and/or robustness.

In a sixth exemplary configuration, a plurality of sensor pods 102 are used, where one or more of the sensor pods 102 are positioned on each side of the user's body. Sensor data 111 is collected and processed from each of the sensor pods 102 and symmetry of power output during physical exertion is determined.

System Functional Components

Acoustic, Electromagnetic, or Pressure Based (Ultrasonic, Laser, PPG, RF) Heart Rate Sensor Sensor pod 102 provides a non-intrusive method of measuring heart rate using acoustic and/or electromagnetic waves, and/or pressure.

Acoustic Sensor (Optional)

Sensor pod 102 may include an acoustic transducer for measuring aspects of a user's heart activity, similar to a phonocardiogram. In an embodiment, sensor pod 102 uses a transducer (e.g., a microphone) to directly measure the sounds created by cardiac activity. Sensor pod 102 may also use the acoustic transducer(s) with an active, controlled source to measure responses that may be collocated with the source, similar to ultrasonic methods. These responses may be used to generate a signal indicative of biological activity, such as pulse rate. Similar techniques include Doppler ultrasound. Regardless of the method by which the signal is measured, the signals may be pseudo-periodic and the signature method of analysis discussed above may be applied.

Motion Processor

One or more sensor pods 102 may incorporate one of (a) a 3-axis (e.g., accelerometer only), (b) a 6-axis (e.g., accelerometer & gyroscope), and (c) a 9-axis (e.g., accelerometer, gyroscope & compass) to generate motion data. Alternatively, one or more sensor pods 102 may include a Global Navigation Satellite System (GNSS) based motion processor that generates motion data. This motion data, however derived, may be used to determine acceleration, orientation, and rotation, and thereby instantaneous motion, of sensor pod 102. Determined motion of sensor pod 102 may be used to assist with the removal of motion artifacts from the heart rate measurement. These motion artifacts are sensed by pod 102 are interpreted as heart rate measurements, for example, but by considering the magnitude and direction of motion of pod 102 using other sensors (and/or other pods), and correlating this motion with the sensed heart rate, correction may be made for artifacts induced by an expected amount of blood sloshing.

Barometric Pressure Sensor

Sensor pod 102 may include a barometric pressure sensor, for example located near a PPG interface on active surface 308, to measure barometric pressure exerted on sensor pod 102.

Skin Temperature Sensor

Sensor pod 102 may include a temperature sensor 110, for example located near a PPG interface on active surface 308, to measure a temperature of a user's skin. Temperature measurement may be useful to determine a user's health (e.g., by detecting an overheating condition) and/or activity level. Temperature measurement may also be used to fine tune a PPG processing algorithm by taking into account circadian rhythms. Temperature measurements may also be used to drive a PPG sensor smartly, such that the PPG sensor is powered off when the pod is not at or near normal body temperature for example.

Galvanic Skin Response (GSR) Sensor

Sensor pod 102 may also include a GSR sensor 110, for example located near a PPG interface on active surface 308, to measure skin moisture. Measured skin moisture and skin temperature may be used to determine on or both of (a) health and/or activity level of the user, and (b) hydration level of the user, and may be further used to fine tune a PPG processing algorithm.

Respiration Sensor (Optional)

Sensor pod 102 may also include a sensor 110 configured to measure a respiration rate of a user.

Acoustic, Electromagnetic, or Pressure Based Blood Glucose Sensor (Optional)

Sensor pod 102 may also include a sensor 110 configured to measure the absorption/scattering of light in the blood at wavelengths correlated with the presence of glucose.

Acoustic, Electromagnetic, or Pressure Based Blood SpO2 (Ballistocardiography or BCG) Sensor (Optional)

Sensor pod 102 may also include a sensor 110 configured to measure the absorption/scattering of light in the blood at wavelengths correlated with the level of SpO2.

Acoustic, Electromagnetic, or Pressure Based Blood Alcohol Level (BAL) Sensor (Optional)

Sensor pod 102 may also include one or more sensors 110 configured to measure the absorption/scattering of light in the blood at wavelengths correlated with the presence of alcohol.

Processing Unit Software Functional Components

Figure 1B:
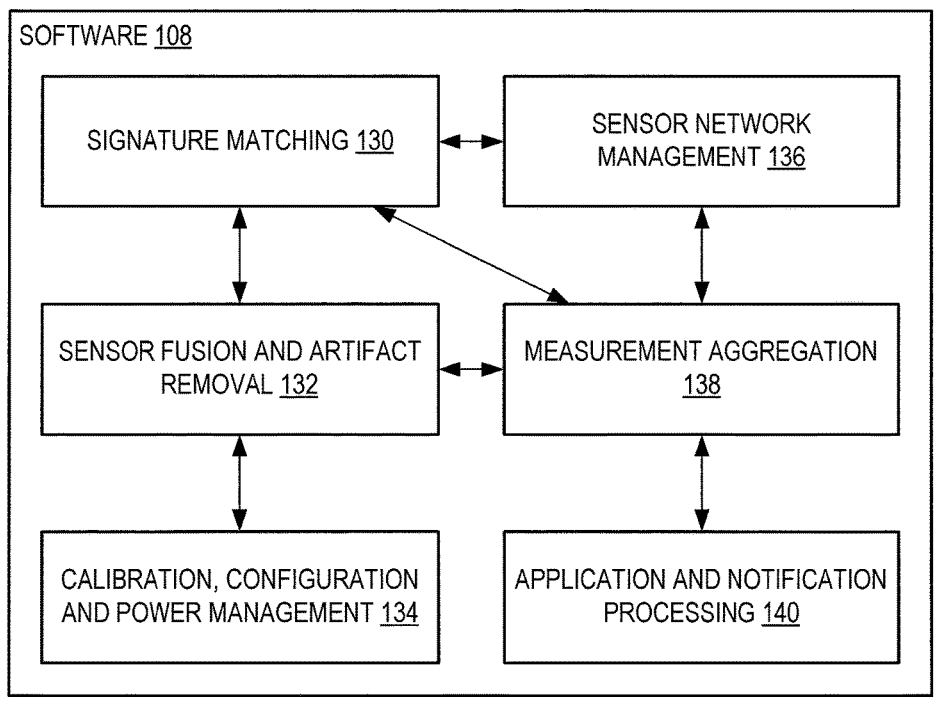
FIG. 1B shows exemplary functionality implemented within the software of FIG. 1, in an embodiment.

FIG. 1B shows exemplary functionality implemented within software 108. Software 108 includes instructions that are executed by processor 104 to implement one or more of sensor matching 130, sensor fusion and artifact removal 132, calibration, configuration and power management 134, sensor network management 136, measurement aggregation 138, and application and notification processing 140.

Calibration, Configuration and Power Management

Sensor pod 102 may be used at one of several positions on the user's body. Calibration, configuration and power management 134 operates to optimize configuration and calibration of sensor pod 102 based upon readings obtained during a calibration phase. The calibration phase is for example performed when sensor pod 102 is first positioned on the user's body. Calibration settings determined during the calibration phase are stored in memory 106 and/or on mobile device 150. In one example of operation, when the user starts using sensor pod 102, mobile device 150 prompts the user to define the location of sensor pod 102 using a dropdown menu. In another example of operation, when the user starts using sensor pod 102, signature matching 130 determines the location of sensor pod 102 based upon accelerometer data collected from sensor 110 and automatically applies appropriate configuration settings.

Sensor Calibration

Sensor pod 102 may implement one or both of Stationary Calibration (SC) and Motion Calibration (MC). Although sensor pod 102 may function without calibration, accuracy may be enhanced when either or both SC and MC is performed. Such calibration may also enhance the efficiency and extend battery life of sensor pod 102. The following examples use PPG, however, other heart rate sensors may be used without departing from the scope hereof. PPG may be used in place of "electromagnetic, acoustic or pressure based heart rate sensors", however the techniques described herein are applicable across many heart rate sensor types.

Overview

The purpose of SC is to identify the "expected peak amplitude" EPA of the sensor waveform in the ideal state. There are two reasons this is of interest: first, during operation, peaks in the sensor waveform that are of a significantly different magnitude from EPA may be excluded from consideration, and second, the power supplied to the sensor (or other parameters affecting the sensitivity) may be altered to bring the EPA within a desired amplitude range (either enhancing accuracy or reducing power requirements). The amplitude value depends upon skin tone, anatomical location and temperature, for example. For a given user, variation in the first two factors indicates that SC is desired for each mounting location. A temperature sensor and simple model may be incorporated within each sensor pod 102 and/or mobile device 150 to obviate the need for SC at each use.

The purpose of MC is to determine correlation between motion, measured by an accelerometer for example, and any motion related artifact within data from one or more other sensors. This is particularly important because sensor pod 102 may be mounted in many different locations where local blood flow may be affected differently by the same motion, and also because each location may undergo different motion during operation.

In an embodiment, calibration information may be averaged over a suitably large number of users for certain key mounting locations such that in the absence of user specific calibration information, the averaged calibration information may be used within sensor pod 102. In situations where more than one pod 102 is used, a weighted Measurement Site Reliability Factor may be applied to indicate which should be "trusted" more in the case of disagreement, or to obtain an optimal solution. For example, one location on the body may have lower expected signal amplitude, while another may have larger motion artifacts. These reliability factors may be obtained from mass calibration and/or enhanced using personal static and motion calibration. Key aspects of this information include: "Scale Factors" that define the relationship between the peak in the motion peak and the corresponding sensor peak, and "Delays" that define the time between a peak in the motion measurement and the corresponding sensor peak. In each case, there are three factors when the motion sensor has three axes.

Although more advanced methods are possible, both of these aspects may be ascertained using a cross-correlation of the sensor and motion signals. The "delay" is the ordinate of the first peak in the cross-correlation, and the "scale factor" may be obtained from the magnitude of the peak.

Static Calibration (SC)

Calibration may be used to adjust for different skin tones (e.g. settings that work for a Caucasian user may not work for a South Asian user). During calibration, sensor pod 102 uses a range of different settings for each sensor type and stores the best ones based upon Signal to Noise Ratio and other metrics. These settings may include LED current, "flash" rate, flash width, and LED color. Where a detector array is included, the most appropriate detector (or combination of them) for use at a particular location may be selected.

Figure 7:
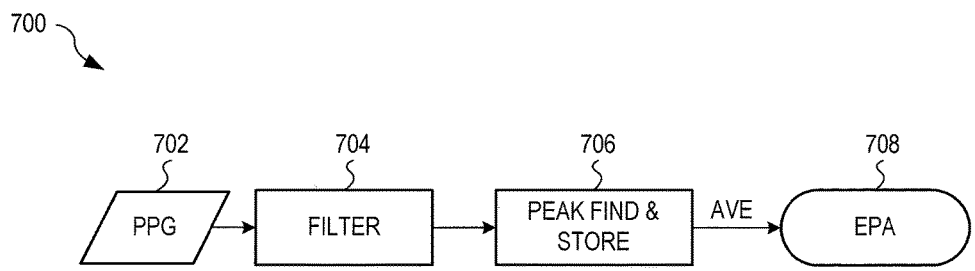
FIG. 7 shows one exemplary method for static calibration of the sensor pod of FIG. 1, in an embodiment.

FIG. 7 shows one exemplary method 700 for static calibration. Method 700 is for example implemented within one or both of pod 102 and mobile device 150. In step 702 of method 700, data is collected from sensor 110 and from motion sensors while the user is motionless. In one example of step 702, while the user is motionless, sensor data 111 is collected within pod 102 from sensors 110 and from sensors 110 within other pods 102 via transceiver 112. In another example of step 702, sensor data 111 is collected within mobile device 150. In step 704 of method 700, a filter (band-pass, identical to that used in operation) is applied to the collected data. In one example of step 704, software 108 implements a band pass filter to process sensor data 111. In another example of step 704, software within mobile device 150 implements a band pass filter to process sensor data 111. In step 706 of method 700, positive peaks preceding zero crossings are determined and stored. In one example of step 706, software 108 implements an algorithm to determine positive peaks preceding zero crossings within the filtered sensor data 111. In another example of step 706, software within mobile device 150 implements an algorithm to determine positive peaks preceding zero crossings within the filtered sensor data 111. In step 708 of method 700, an average of the peak amplitudes over the calibration period is determined and stored as the EPA. In one example of step 708, software 108 implements an algorithm to determine and store an average of the peak amplitudes over the calibration period. In another example of step 708, software within mobile device 150 implements an algorithm to determine and store an average of the peak amplitudes over the calibration period.

Figure 8:
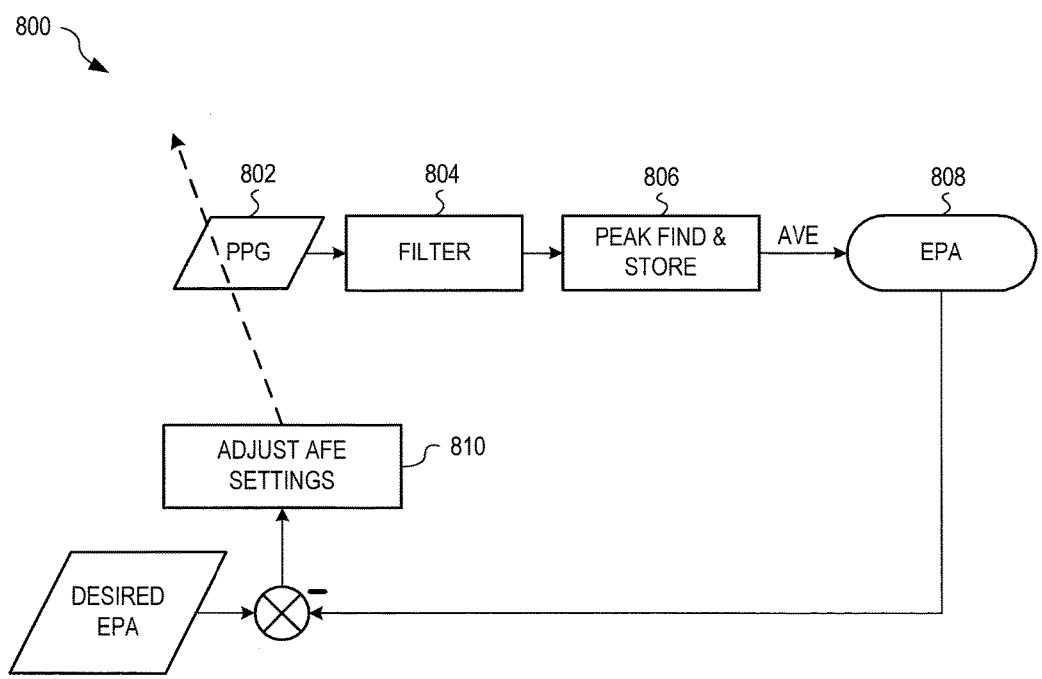
FIG. 8 shows one exemplary method for static calibration with feedback (SCF) of the sensor pod of FIG. 1, in an embodiment.

FIG. 8 shows one exemplary method 800 for static calibration with feedback (SCF). Method 800 is for example implemented within one or both of pod 102 and mobile device 150. In step 802 of method 800, data is collected from sensor 110 and from motion sensors while the user is motionless. In one example of step 802, while the user is motionless, sensor data 111 is collected from sensors 110 within pod 102 and optionally from sensors 110 within other pods 102 via transceiver 112. In another example of step 802, sensor data 111 is collected within mobile device 150 from sensors 110 within one or more pods 102.

In step 804 of method 800, a filter (band-pass, identical to that used in operation) is applied to the collected data. In one example of step 804, software 108 implements a band-pass filter to process sensor data 111. In another example of step 804, software within mobile device 150 implements a band-pass filter to process sensor data 111. In step 806 of method 800, positive peaks preceding zero crossings are determined and stored. In one example of step 806, software 108 implements an algorithm to detect and store positive peaks preceding zero crossings within sensor data 111. In another example of step 806, software within mobile device 150 implements an algorithm to detect and store positive peaks preceding zero crossings within sensor data 111.

In step 808 of method 800, an average of the peak amplitudes over the calibration period is determined and stored as the EPA. In one example of step 808, software 108 implements an algorithm to determine and store an average of the peak amplitudes over the calibration period. In another example of step 808, software within mobile device 150 implements an algorithm to determine and store an average of the peak amplitudes over the calibration period. In step 810 of method 800, the settings of the sensor and/or associated analog front end (AFE) are adjusted until a desired EPA is achieved. In one example of step 810, software 108 adjusts settings of sensor 110 and/or and associated analog front end (AFE) of sensor 110 are adjusted until a desired EPA is achieved. In another example of step 810, software within mobile device 150 sends a command to one or more pods 102 to adjusts settings of sensor 110 and/or and associated analog front end (AFE) of sensor 110 until a desired EPA is achieved.

Motion Calibration (MC)

Figure 9:
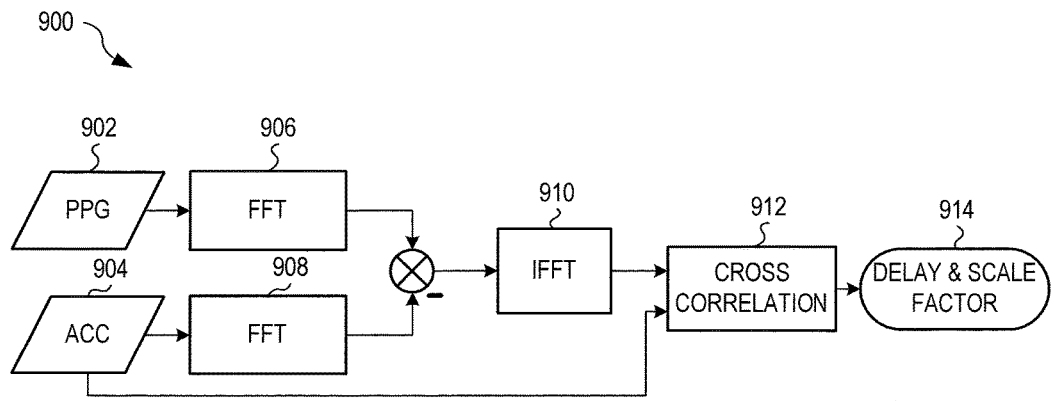
FIG. 9 shows one exemplary method for motion calibration of the sensor pod of FIG. 1, in an embodiment.

FIG. 9 shows one exemplary method 900 for motion calibration of sensor pod 102. Method 900 is for example implemented within calibration, configuration and power management 134 of software 108. During an MC phase, the user enters calibration mode (e.g., by interacting with mobile device 150) and indicates that the MC phase should start (e.g., by pressing a start-button on same interface of mobile device 150). Then the user remains motionless for a short period (5 seconds for example), then undergoes periodic motion(s) that are likely to be execute while using sensor pod 102. Sensor data 111 is captured during a short period of such motion (e.g. 5 seconds) and recording automatically terminates. Processing of the recorded data using method 900 then begins.

Steps 902 and 904 of method 900 may occur concurrently. In step 902, method 900 collects sensor data 111 from sensors 110. In one example of step 902, sensor data 111 from sensors 110 is collected and stored within memory 106. In step 904, method 900 collects sensor data 111 from movement sensors (e.g., accelerometers) to determine a motion waveform. In one example of steps 902 and 904, sensor data 111 from sensors 110 is collected and stored within memory 106. Steps 906 and 908 may occur concurrently or occur sequentially. In step 906, method 900 processes sensor data 111 from step 902 using a fast Fourier transform. In step 908, method 900 processes sensor data 111 from step 904 using a fast Fourier transform. In one example of steps 906 and 908, calibration, configuration and power management 134 implements a fast Fourier transform to process sensor data 111.

In step 910, method 900 performs an inverse fast Fourier transform on the difference between the outputs of steps 906 and 908. In one example of step 910, calibration, configuration and power management 134 implements an inverse fast Fourier transform on differences between the outputs of steps 906 and 908. Steps 906 through 910 thereby eliminate the pulsatile aspect of the sensor waveform from the motion waveform to generate a modified sensor waveform. The pulsatile aspect of the sensor waveform is eliminated so that it does not adversely affect the calibration. In step 912, method 900 performs a cross-correlation between the motion waveform and the modified sensor waveform. In one example of step 912, calibration, configuration and power management 134 implements a cross-correlation between the motion waveform and the modified sensor waveform.

In situations where the MA is much larger than the pulsatile part of the sensor signal, steps 906 through 910 may be omitted (i.e., the cross-correlation of the accelerometer and PPG signals may be performed directly). In an alternate embodiment, when elimination is necessary, adaptive noise cancellation may be used, where a repeated version of the motionless sensor signal is used as reference.

Operation Overview

Figure 10:
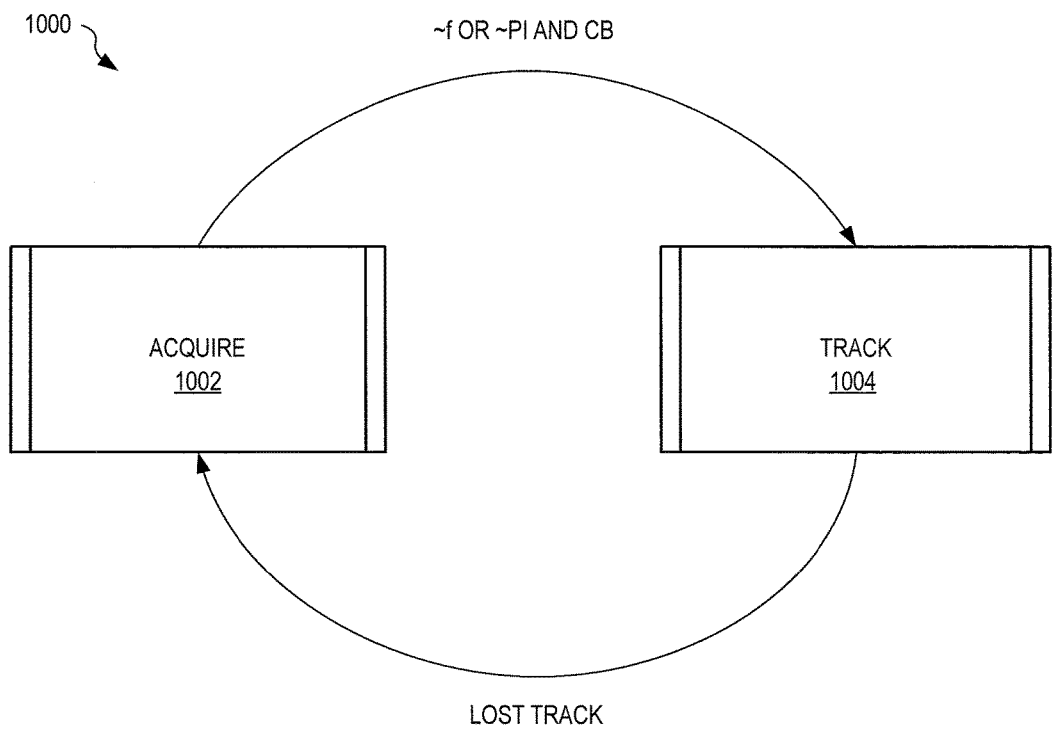
FIG. 10 shows one exemplary method for determining a pulse-rate (PR) of a user using a two-step process with the sensor pod of FIG. 1, in an embodiment.

FIG. 10 shows one exemplary method 1000 for determining a pulse-rate (PR) of a user using a two-step process. Method 1000 is implemented in sensor fusion and artifact removal module 132 of software 108 for example. In step 1002, method 100 acquires a clean beat signal from sensors 110. In one example of step 1002, software 108 implements an algorithm to detect a clean beat signal within sensor data 111. In step 1004, method 1000 tracks the identified beat in the sensor signal. In one example of step 1004, software 108 implements an algorithm to track beats within sensor data 111.

Method 1000 is similar in spirit to the functioning of a single channel GPS receiver. During Acquisition in step 1002, the approximate PR is calculated and a "clean beat" is identified. A "clean beat" is a peak in the sensor waveform that has the expected morphology and that does not coincide (within the time-period obtained during calibration with a peak in the accelerometer signal. After acquisition in step 1002, step 1004 confines attention to periodic windows of sensor and accelerometer data starting at a "clean beat" with period equal to the estimated pulse interval and widths reflecting the confidence in that estimate. The pulse-rate is regularly updated by averaging time between "clean beats" identified in these windows. If there is too-long a time between observing subsequent clean beats, then the functionality switches back to acquisition. In particularly harsh environments, it may be expected that the bulk of the time will be spend in acquisition. The benefit of the Tracking portion is that it is less computationally intensive and will normally allow a higher accuracy estimate of the PR.

Acquisition

Acquisition may be determined in two steps: (a) estimating the PR or pulse interval (PI), and (b) Identifying a "clean beat" (CB). The approximate PR or PI can be found by a variety of methods. Performing the autocorrelation on a batch of data, and then finding the ordinate of the first peak can give the PI. Frequency domain methods may also be used to estimate PR. For example an FFT on a sample of data may be used. The resolution of the estimate depends upon the duration of the sample.

Figure 11:
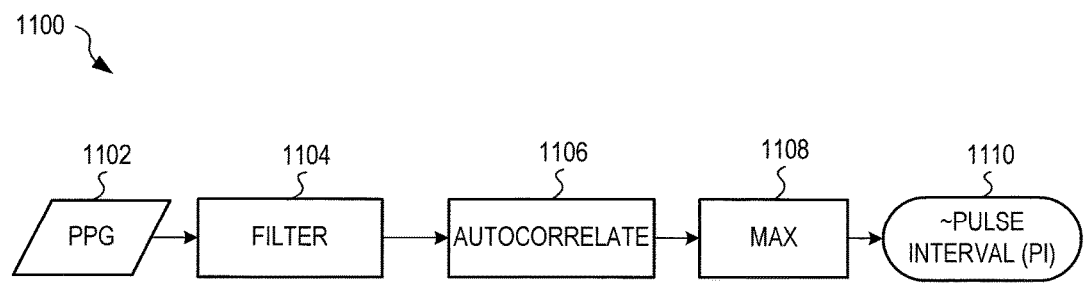
FIG. 11 shows one exemplary method for implementing the acquisition of the method of FIG. 10, in an embodiment.
Figure 12:
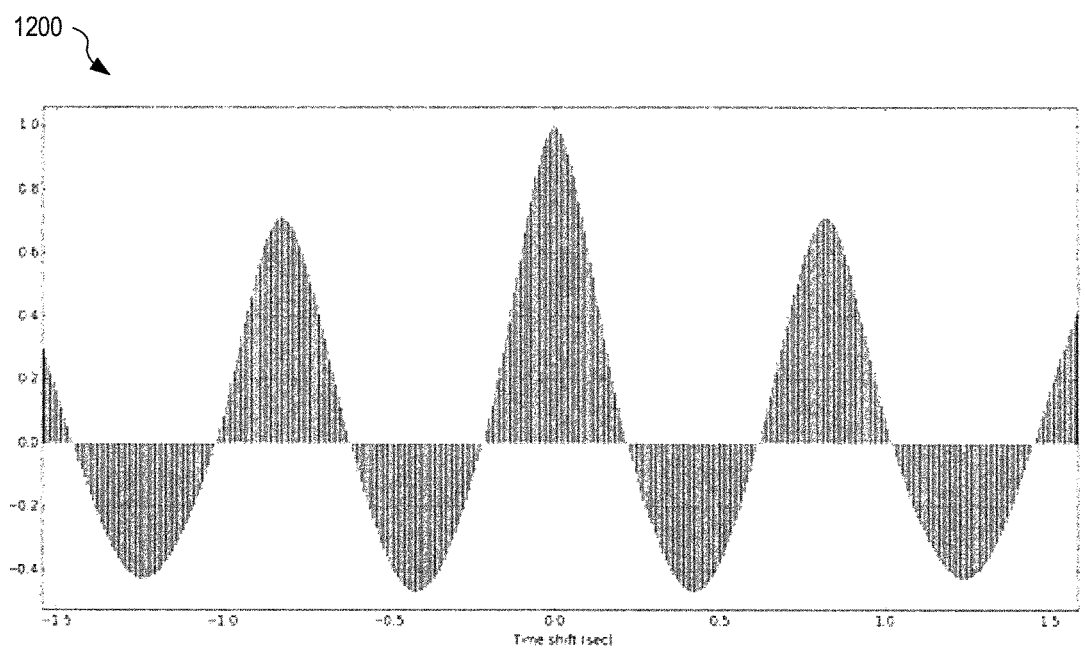
FIG. 12 is a graph illustrating exemplary autocorrelation of a sample of PPG signals from the sensor pod of FIG. 1, in an embodiment.

FIG. 11 shows one exemplary method 1100 for implementing the acquisition in step 1002 of method 1000, FIG. 10. Method 1100 is for example implemented within sensor fusion and artifact removal module 132 of software 108. FIG. 12 is a graph 1200 illustrating exemplary autocorrelation of a sample of PPG signals from sensor pod 102. A position of a maximum within the autocorrelation allows an approximate period to be determined, as used for acquisition of step 1002 of method 1000. In the example of FIG. 12, autocorrelation of a 5 second sample of sensor data 111 gives an indicated pulse interval (PI) at around 0.8 seconds. FIGS. 11 and 12 are best viewed together with the following description.

In step 1102, method 1100 collects sensor data 111 from sensor 110. In one example of step 1102, software 108 receives and stores sensor data 111 in memory 106. In step 1104, method 1100 applies a filter to the collected data. In one example of step 1104, software 108 implements a filter to process sensor data 111. Step 1104 may also, or alternatively, apply other techniques such as adaptive noise cancellation to reduce motion effects. In step 1106, method 1100 performs an autocorrelation on the filtered data of step 1104. In one example of step 1106, software 108 implements an autocorrelation algorithm to process sensor data 111. In step 1108, method 1100 determines the ordinate of the first peak. In one example of step 1108, an algorithm implemented within software 108 determines an ordinate of the first peak output from step 1106. In step 1110, method 1100 determines a PI based upon the ordinate of the first peak. In one example of step 1110, software 108 implements an algorithm to determine a PI based upon the ordinate of the first peak.

Figure 13:
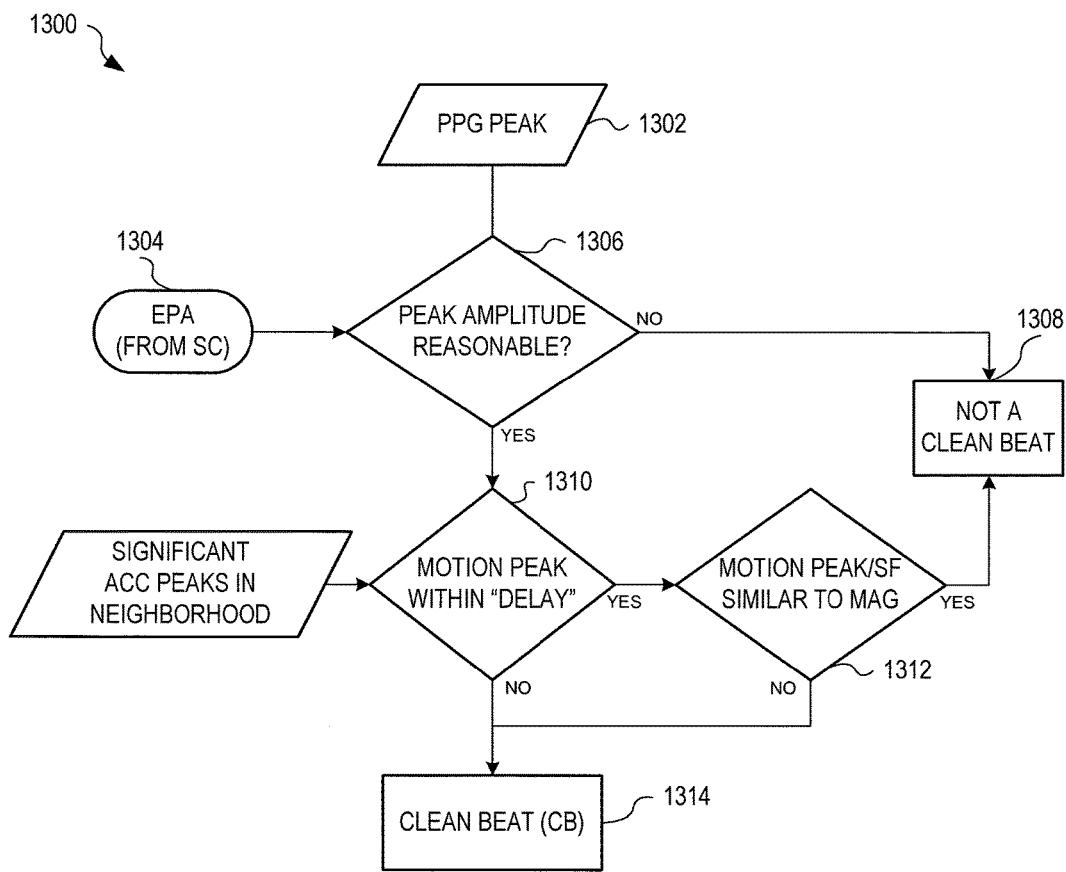
FIG. 13 is a flowchart illustrating one exemplary method for identifying a clean beat (CB) within the sensor pod of FIG. 1, in an embodiment.

FIG. 13 is a flowchart illustrating one exemplary method 1300 for identifying a clean beat (CB). Method 1300 is for example implemented within software 108. Identification of a CB makes use of the calibration parameters (if present) and motion sensor data. Each peak in the sensor data is evaluated in turn. In step 1302, method 1300 identifies a next peak in the PPG sensor data. In one example of step 1302, the algorithm within software 108 determines a next peak in sensor data 111. Sensor data 111 may be filtered, but has not been otherwise used, since each new peak is evaluated in turn. In step 1304, method 1300 determines the EPA from the SC. In one example of step 1304, software 108 implements an algorithm to determine the EPA from the SC.

In step 1306, method 1300 compares the magnitude of the peak from step 1302 to the EPA of step 1304. In one example of step 1306, software 108 implements a comparison to evaluate the peak from step 1302 to the EPA of step 1304. If, in step 1306, method 1300 determines that the sensor peak is reasonable (i.e., not too big and not too small by factors either way to account for expected variation) method 1300 continues with step 1310; otherwise, method 1300 continues with step 1308. In step 1308, the peak identified in step 1302 is rejected and not being a clean beat. In one example of step 1306, software 108 implements thresholds to evaluate reasonableness of whether the peak is to large or too small.

In step 1310, method 1300 determines whether a motion peak is within the delay obtained during MC. In one example of step 1310, software 108 implements an algorithm for determining whether a motion peak is within the period defined by the delay obtained during MC. If, in step 1310, method 1300 determines that the motion peak is within the delay, method 1300 continues with step 1312; otherwise method 1300 continues with step 1314.

If, in step 1312, method 1300 determines that the scale factor obtained during MC roughly accounts for the peak, then method 1300 continues with step 1308; otherwise method 1300 continues with step 1314. In step 1314 method 1300 identifies the peak of step 1302 as a clean beat (CB).

To initiate the algorithm, a simple peak finding method is used to find a peak in the PPG signal (1302). The amplitude of this peak is compared (1306) against known peak amplitudes that are expected (1304). If the peak does not pass this test, it is identified as not a clean beat (1308). A new PPG peak candidate is then needed. If, however, a clean beat candidate is found, a second test is initiated to determine if a significant accelerometer peak has been located in the vicinity of the PPG peak (1310). If the result of this test is false, a clean beat has been identified (1314). If, however, a significant accelerometer peak is identified in the region of the PPG, a test is performed to determine if the magnitude of the accelerometer peak is significant compare to the PPG peak (1312). If the accelerometer peak is significant, then it is identified as not a clean beat (1308). If the accelerometer peak is insignificant relative to the PPG signal, then a clean beat has been found (1314).

Tracking

Upon receipt of the approximate PR and CB from successful completion of the Acquisition phase, tracking begins. The process involves identification of peaks (and perhaps other morphological parameters (MP)) within short windows of data. The first window is centered at the estimated pulse-interval (PI) from the CB and is of a width that reflects confidence in the estimate, e.g. PI/8. FIG. 14 is a graph 1400 illustrating an identified first peak 1402 within sensor data 111 from sensor 110 and a window 1404, within which a next peak is expected. Within window 1404, peaks and perhaps other MP are identified in the sensor and motion sensor data. If a peak is identified in the window 1404 then the calibration data is used to determine whether it is a CB, using a method similar to Acquisition. If a CB is identified, then the interval between it and the previous CB is stored, the PI is updated (using a weighted average), and the process continues. When the PR is requested by the application, it is based upon an average of the recently calculated intervals.

If a CB is not found in window 1404 (e.g., because there was too much motion), then attention is switched to a following window (e.g., 2*PI from the last CB, etc.). If identification of a CB fails for a given number of intervals within a certain time, e.g., of the last 10 considered windows only 2 CB were found, operation reverts to acquisition.

Configuring the Notification

Calibration, configuration and power management 134 may also create one or more of: (a) customized LED color & flash patterns, (b) heat source temperature, (c) electric shock intensity/pattern, (d) audible tones and (e) vibration rhythms, and assign each to a certain type of notification generated by sensor pod 102 based upon a selection criteria from specified person, of a specified notification type, of specified importance, if the user's phone is in silent mode or not, if a measurement (e.g. heart rate) in the message is above/below a specified threshold, if the measurement in the message is inside or outside of a certain range, if a wireless connection is lost, an incoming tweet or social media message from a specified user, an incoming tweet or social media message matching a specified criteria, incoming phone call, incoming email, other app notifications, etc.

FIG. 15 shows one exemplary table 1500 illustrating exemplary customizations of biofeedback sources. These customizations are described in further detail below.

Customizable Vibration

A user may customize one or more of frequency, intensity, duration, and rhythm of vibration patterns generated by sensor pod 102 for certain types of notification. Notifications may include incoming calls, incoming text messages, incoming email messages, alarms, alerts, and so on, that are generated by mobile device 150. Sensor pod 102 receive and respond to these notifications from mobile device 150 based upon user configuration. In an embodiment, software running on mobile device 150 allows the user to customize which notifications sensor pod 102 responds to, and which vibration pattern to use for these notifications. Where mobile device 150 lacks notification filtering, sensor pod 102 may communicate with the software running on mobile device 150 to receive additional details of an incoming notification to determine whether the notification meets the user-specified filtering criteria.

In one example of operation, a user configures sensor pod 102 to vibrate with three quick beats in response to receiving a notification of an incoming phone call from a specific caller. In this example, mobile device 150 does not have the ability to apply a filter to incoming calls based upon the caller ID, and therefor only sends a notification indicating that there is an incoming call. Upon receiving this notification, sensor pod 102 queries software running on mobile device 102 to obtain caller information and thereby determines whether the incoming call meets the user-specified filtering criteria.

LED Pattern Editor

Sensor pod 102 allows a user, interacting with mobile device 150 for example, to create, edit, preview, and share LED blink patterns.

Vibration Pattern Editor

Sensor pod 102 allows a user, interacting with mobile device 150 for example, to create, edit, preview, and share vibration patterns.

Audio Sequence Editor

Sensor pod 102 allows a user, interacting with mobile device 150 for example, to create, edit, preview, and share audio sequences.

Pattern/Sequence Selector

Sensor pod 102 allows a user, interacting with mobile device 150 for example, to select one or more of an LED blink pattern, a vibration pattern, and an audio sequence to be triggered by one or more events. FIG. 16 shows a table 1600 defining exemplary notification sources and filter criteria that may be configured with one or both of mobile device 150 and sensor pod 102.

Sensor Network Management

When two or more sensor pods 102 are configured to provide concurrent measurements (e.g., based upon sensor data 111) from the same body, sensor network management 136 manages pairing and data connectivity between these sensor pods to allow the measurements to be transferred from one sensor pod 102 to another sensor pod 102 and/or mobile device 150. A weighted measurement site reliability factor may be applied to indicate which should be "trusted" more in the case of disagreement, or to obtain an optimal solution. For example one location on the body may have lower expected signal amplitude, while another may have larger motion artifacts. These reliability factors may be obtained from mass calibration and/or enhanced using personal static and motion calibration.

Figure 19:
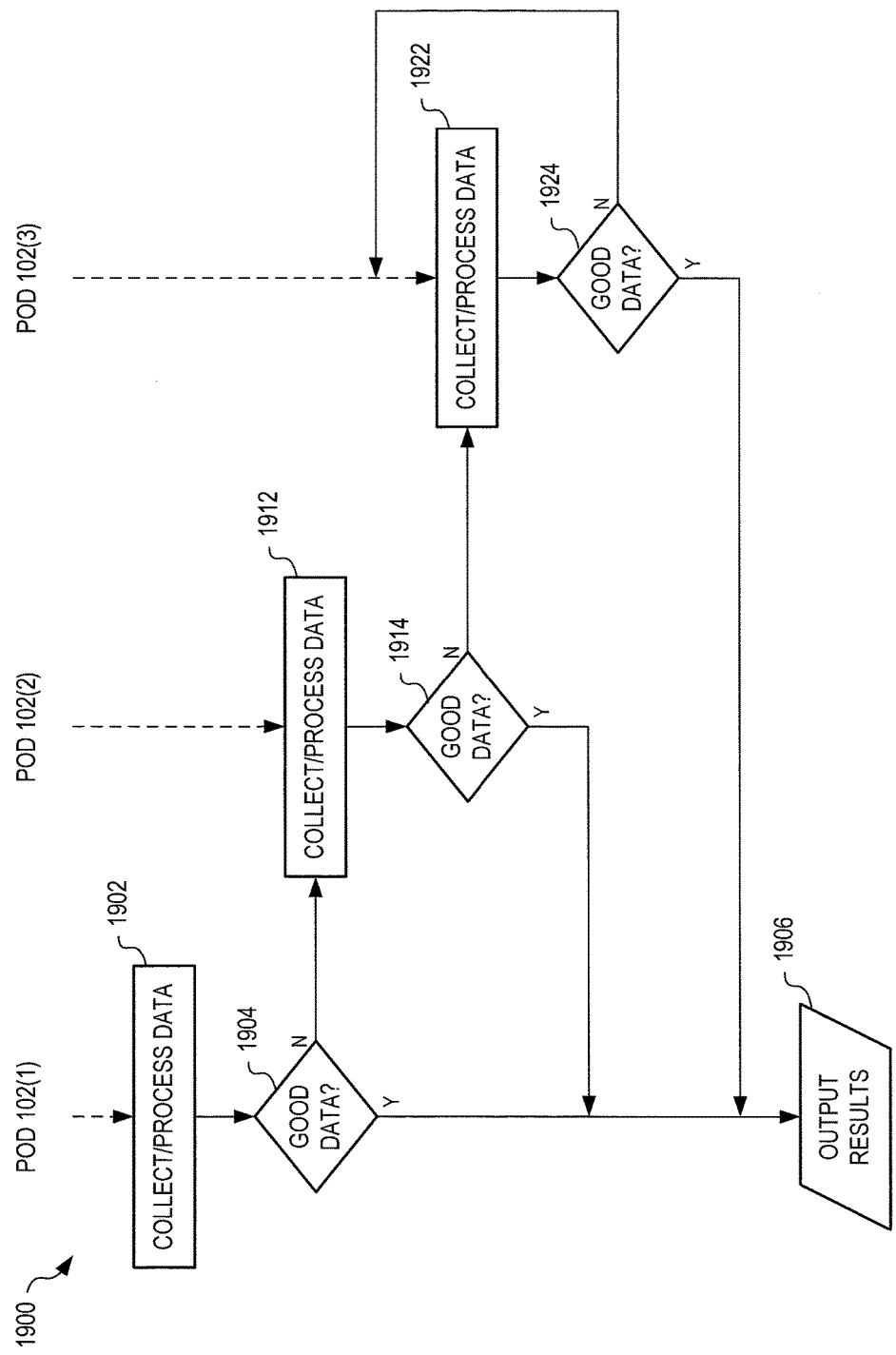
FIG. 19 shows one exemplary scenario illustrating collection and processing of sensor data using three of the pods of FIG. 1, in an embodiment.

FIG. 19 shows one exemplary scenario 1900 illustrating collection and processing of sensor data using three pods 102(1), 102(2) and 102(3) of FIG. 1. In step 1902, pod 102(1) collects and processes sensor data. In one example of step 1902, pod 102(1) may be worn on a wrist of a user and operated to collect accelerometer data that is processed to determine a count of steps taken by the user. Step 1904 is a decision. If, in step 1904, the collected and processed data of step 1902 is analysed to determine whether the data is good. For example, if a signal to noise ratio in the spectrum of the data collected and processed in step 1902 is above a predefined threshold, the data may be considered as good. If the data is good, the results are output in step 1906.

If the data is not good, pod 102(2) collects and processes data in step 1912. In example of step 1912, pod 102(2) is worn on the waist of the user and also collects and processes accelerometer signals for counting steps. Step 1914 is a decision. If, in step 1914, the data is good, the data is output in step 1906. If the data is not good, data is collected in processed in step 1922 by pod 102(3). For example, pod 103(3) is worn on a foot of the user and operates to collect and process accelerometer data to count steps. Step 1924 is a decision. If, in step 1924 the data is determines as being good, the data is output in step 1906. If the data is not good, the process is tried again.

Figure 20:
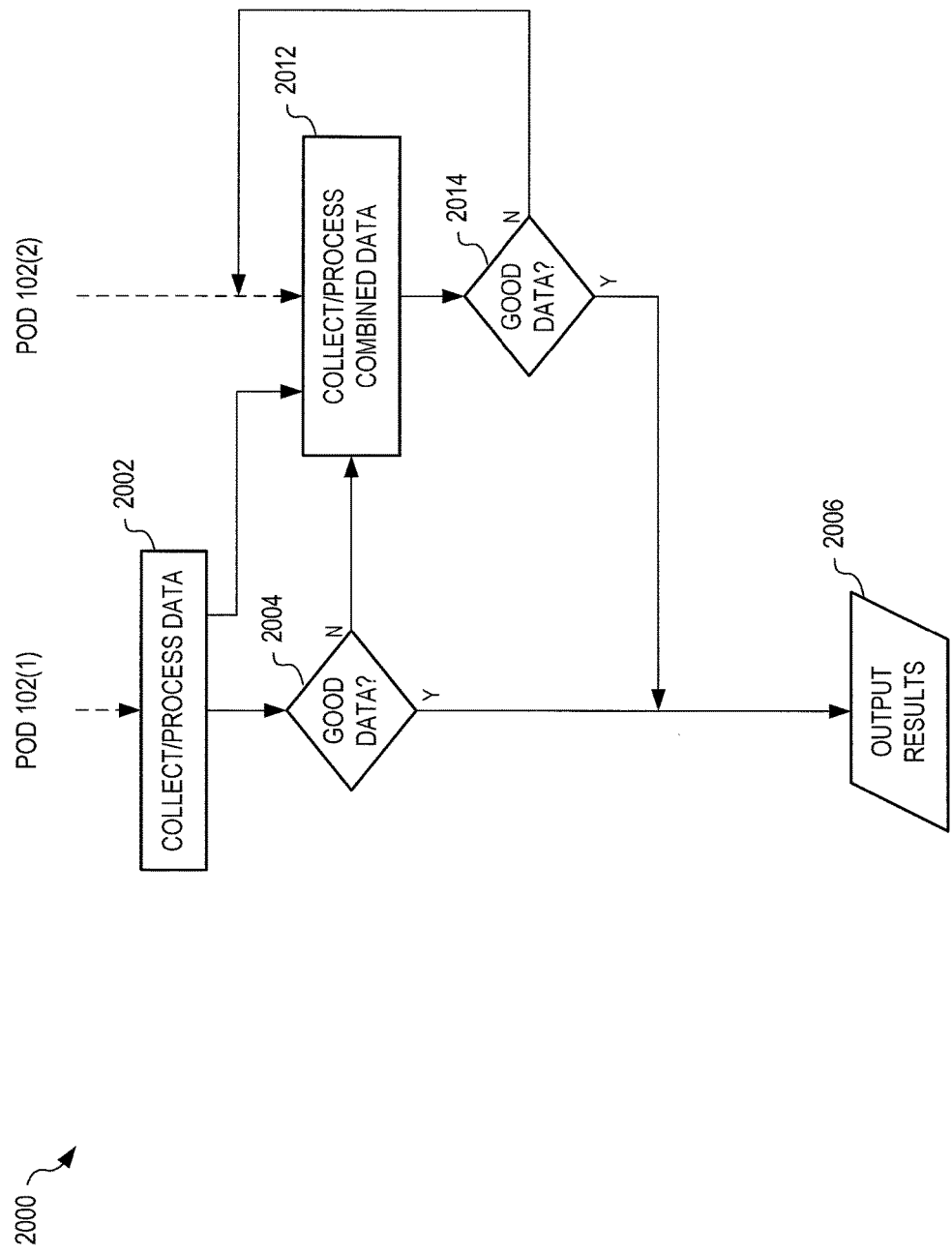
FIG. 20 shows one exemplary scenario illustrating collection and processing of sensor data using two of the pods of FIG. 1, in an embodiment.

FIG. 20 shows one exemplary scenario 2000 illustrating collection and processing of sensor data using two pods 102(1) and 102(2) of FIG. 1. In step 2002, pod 102(1) collects and processes sensors data. In one example of step 2002, pod 102(1) is positioned on a wrist of a user and operates to collect and process data from an accelerometer to determine a count of steps taken by the user. Step 2004 is a decision. If in step 2004 the data is determined as good, the data is output in step 2006. If step 2004 determines that the data is not good, the sensor data of step 2002 is combined in step 2012 and processed with data collected by pod 102(2). In one example of step 2012, pod 102(2) is attached to a foot of the user and collects and processes accelerometer data to determine a count of steps by the user. Step 2014 is a decision. If, in step 2014, the combined data is determined as good, the results are output in step 2006. By combining the data from step 2002 with collected data of step 2012, strong peak accelerations detected from foot falls by pod 102(2) may be used to better identify peaks within data collected in step 2002 (from the wrist position). Thus, pod 102(1) may be trained to better identify foot step patterns in data collected from the wrist accelerometer based upon data from the foot sensor. If, in step 2014, the data is not good, more data is collected and processed to identify patterns indicative of user steps.

Signature Matching

When measuring heart rate for example, sensor 110 produces a signal (e.g., sensor data 111) that is instantaneously related to the degree of perfusion at the location of the sensor. Since this signal is largely periodic, it is amenable to the concept of signature matching 130.

Sensor Fusion and Artifact Removal

When measuring heart rate for example, major disturbances to the periodic signal from sensor 110 are due to motion artifacts, which themselves may be described/identified as a signature. For example, if sensor pod 102, and thereby sensor 110, is located on a wrist of the user, motion artifacts caused by the user swinging the associated arm during gait is superimposed on the signal indicative of the pulse. Both parts of the signal may be identified as signatures and used within sensor pod 102. For example, identified motion artifacts may be removed, by artifact removal 132 for example, from the heart rate signal to improve accuracy and reliability of determined heart rate, and the identified motion artifact may be used to infer a motion state of the user.

PPG as Calibration Source for Ultrasonic/Acoustic Signatures

Within sensor pod 102, PPG sensor (e.g., sensor 110) measurements may be used as a reference for learning and calibrating a signature based upon sensor data 111 received from ultrasonic and/or acoustic sensors (e.g., sensor 110) when sensor pod 102 is held against the user's skin. That is, the PPG sensor may be activated as needed only to calibrate signals from the acoustic sensor, leaving the PPG circuitry mostly powered down, thus increasing battery life as compared to when the PPG sensor is continually activated, whilst maintaining accuracy and confidence in heart rate determined from the acoustic sensor.

Measurement Aggregation

When multiple sensor pods 102 are held against the skin of the same body (e.g., a user has several sensor pods 102 at different positions on his/her body), measurement aggregation 138 aggregates the sensor measurements from each sensor pod 102 to determine one or more of: (1) an aggregated value, using least squares error or other method, (2) an aggregated measurement quality factor, by examining how many individual pod measurements fall within a certain error radius from the aggregated value, and (3) an individual measurement quality factor, by examining the error radius between each individual measurement and the aggregated value.

Application and Notification Processing

Application and notification processing 140 may execute one or more applications that consume local or network transported sensor measurements (e.g., sensor data 111) and/or notifications from mobile device 150 to generate local, and/or network transported, notifications and data.

Geriatric Balance with Vibration Feedback

Sensor pod 102 may be used to predict and warn of a fall by a geriatric user. Sensor pod 102 may also be used to identify when a fall has occurred.

Fall Prediction

In geriatric patients in particular, there is a small number of circumstances when a large number of falls occur. For example, falls occur then a geriatric patient is rising from a sitting position. Such motion is easily recognized using inertial sensors 110 within sensor pod 102 positioned on the geriatric patient. When such motion results in a fall, it is often accompanied by a drop in blood pressure of the geriatric patient. This, sensor pod 102 may predicts such a fall using PPG and/or other heart rate sensors 110. Specifically, when software 108 within sensor pod 102 detects a combination of rising motion and a change in blood pressure, sensor pod 102 generates a notification to alert the geriatric patient of an impending fall, thereby allowing them to take evasive action.

Fall Identification

Identification of a fall is a simpler problem that has seen a lot of coverage in academic papers. Sensor pod 102 may be configured to identify an impact (as the geriatric patient hits the ground) and qualifying this detection by estimating the orientation of the patient through inspection of accelerometer signals from sensor 110 to verify that the patient has fallen. Sensor pod 102 may be configured to communicate with mobile device 150 and call emergency services and/or any other appropriate contact. Optionally, sensor pod 102 communicates with a server 170, via mobile device 150, to raise an alarm, where server 170 is maintained by a monitoring service.

A Learning System for Fall Prediction

Software 108 within sensor pod 102 may be configured to learn from collected sensor data 111 such that over time, detected falls may be used to update and improve future prediction/warning aspects. For example, sensor pod 102 may learn which situations are most correlated to falls, using a signature learning process. This learning may be assisted by user intervention under instruction from sensor pod 102, for example by detecting when a user provides an indication (e.g., a tap/double-tap or some other indication on sensor pod 102) of when they feel at risk of a fall. Sensor pod 102 may create and/or modify any signature it uses to detect future conditions that are similar to conditions when the user felt at risk of a fall.

Activity Monitoring Using Multiple Sensors

Software 108 may include an algorithm for estimating a user's activity level, real caloric burn, and so on, by taking into account one or more of heart rate data, motion data, galvanic skin response data, temperature data, $O_2$ saturation data, and blood glucose data from one or more sensor pods 102, and/or one or both of GNSS data and temperature data from mobile device 150. The estimated user activity and/or real caloric burn may be transmitted to mobile device 150 for display to the user and/or transmitted to other compute devices. Accuracy may be enhanced by aggregating data from multiple sensor pods 102 worn at different places on the user's body.

Figure 17:
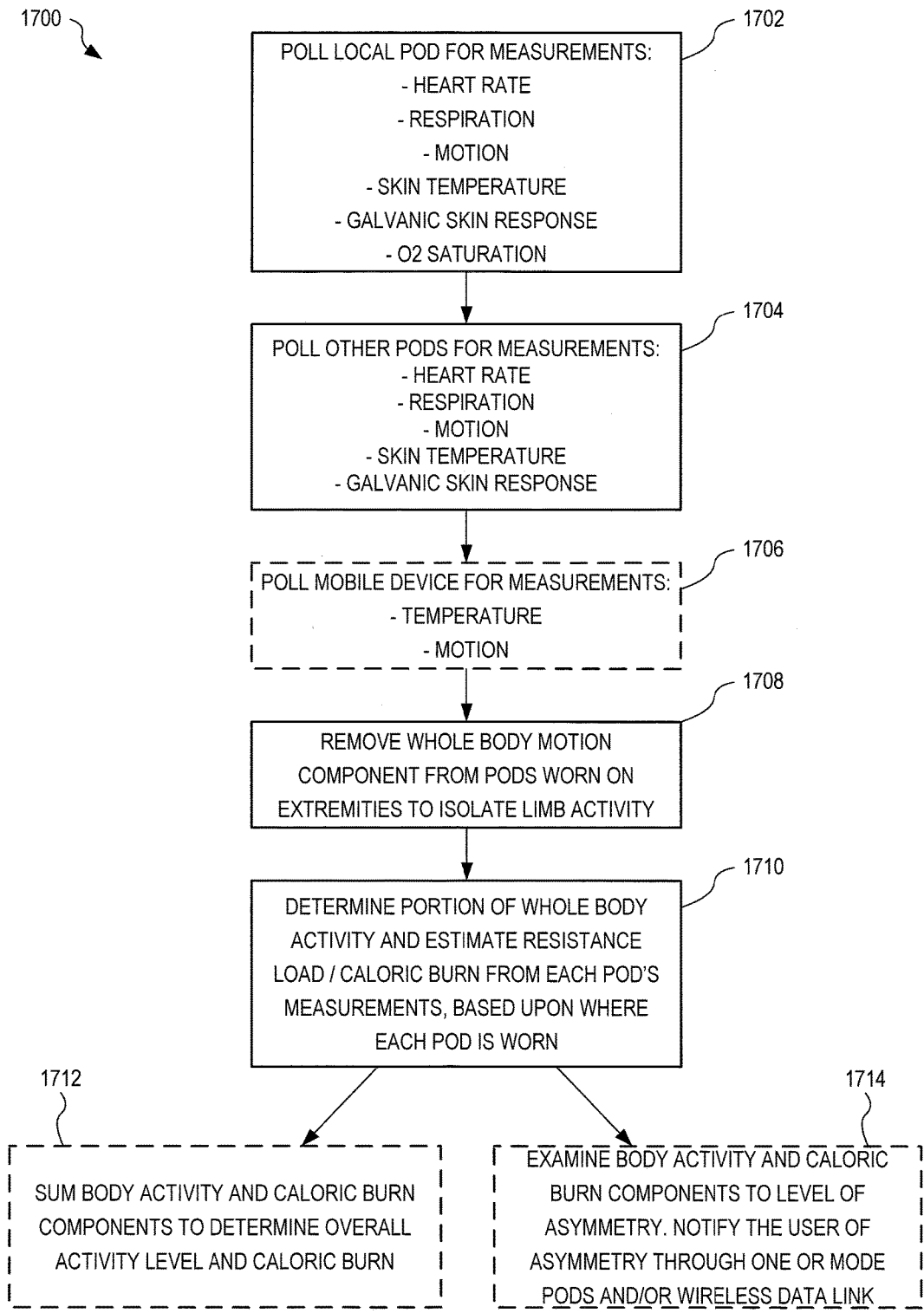
FIG. 17 is a flowchart illustrating one exemplary method for monitoring activity of a user using multiple sensor pods of FIG. 1, in an embodiment.

FIG. 17 is a flowchart illustrating one exemplary method 1700 for monitoring activity of a user using multiple sensor pods 102. Method 1700 is for example implemented within software 108 of one sensor pod 102. In step 1702, method 1700 polls sensors 110 within the local sensor pod 102 to determine one of heart rate, respiration, motion, skin temperature, galvanic skin response, and $O_2$ saturation. In step 1704, method 1700 polls other sensor pods 102 to determine one of heart rate, respiration, motion, skin temperature, galvanic skin response, and $O_2$ saturation. Step 1706 is optional. If included, in step 1706, method 1700 polls mobile device 150 to determine one or both of temperature and motion. In step 1708, method 1700 removes whole body motion component from sensor data 111 from each sensor pod 102 worn on an extremity to isolate limb activity. In step 1710, method 1700 determines a portion of whole body activity and estimates resistance load and/or caloric burn for each sensor pod 102 based upon sensor data and location of that sensor pod on the user.

Method 1700 has two options shown in steps 1712 and 1714. Step 1712 or step 1714 may be selected based upon a desired output from sensor pod 102. Optionally, both steps 1712 and 1714 may be performed to determine both outputs.

In step 1712, method 1700 sums body activity and caloric burn components to determine an overall activity level and caloric burn.

Body Symmetry Monitor and Coaching

In step 1714, method 1700 examines body activity and caloric burn components to determine a level of asymmetry and then notifies the user of any asymmetry through one or more of the sensor pods and/or mobile device 150 via wireless data link. This application aggregates sensor measurements from two or more sensor pods 102 (each with haptic feedback), worn at various points on the body (arms, chest, legs, hands, feet). Step 1714 of method 1700 analyzes sensor data to determine if the left side of the body is outputting the same or more power as the right side and vice versa. Haptic feedback from one or more sensor pods 102 informs the user in real-time any determined asymmetry. For example, one sensor pod 102 positioned on a limb determined to have reduced activity and/or caloric burn may be notified to vibrate to indicate that more effort is required in that limb. In addition to power output, this same approach may be used for comparing left vs. right foot contact time on the ground, swim stroke style, gait, length of movement, balance, and so on.

Programmable Unobtrusive Communicator

In an embodiment, sensor pod 102 is configured to wait for a specific notification to be received from mobile device 150 (or other communication device) via a wireless data link. Upon receiving the specific notification, sensor pod 102 generates haptic (or other) output to notify the user. Thus, one or more sensor pods 102, each containing haptic or other notification mechanisms, may be signaled by mobile device 150 (e.g., an app running on a smartphone) to cue a wearer of the sensor pod to perform synchronized actions. Since sensor pod 102 is small and discreet, users may be cued without discovery by third party observers. Such cuing may be used for one or more of: (1) a start signal for flash mob or performing group, (2) a synchronized metronome, (3) a signal to all members of a squadron or platoon to take a certain strategic direction in an operation or battle, (4) a signal to members of a sports team the strategic direction of a coach or trainer at the sidelines, and (5) a signal for players on a curling team to start or stop sweeping the ice in front of the moving rock.

Concussion Analysis

One or more sensor pods 102 may be used for concussion analysis of a user. Software 108 includes an application/algorithm that aggregates sensor measurements from the one or more sensor pods 102 arranged on the head and body of the user to determine impact trauma based upon sensor data 111 from each pod. In an embodiment, these sensor pods 102 monitor cumulative trauma to head or body over the course of time (e.g. the duration of a sporting event or game for a team player), and then notify a coach (e.g., wirelessly) when a specified cumulative trauma level has been reached by the user. The coach is thereby aware that it may be wise to remove the player from game play for the remainder of the event to prevent serious injury. In another embodiment, the one or more sensor pods 102 include an algorithm for monitoring impact to the user's body and head and determining an effect of whiplash on the neck of the user.

Real-Time Grade Adjusted Training Zones

Two or more sensor pods 102 may be positioned at a known points and orientations on a bicycle. Sensor data 111 from these sensor pods 102 is used to determine the grade of incline that the bicycle is on. Each sensor pod 102 determines orientation of the sensor pod by examining the direction of gravitational acceleration when the bicycle is on flat terrain. Changes in direction of gravitational acceleration as the bicycle enters an incline are then used to measure the grade of the incline, and one or both of the sensor pods 102 may take one of or more of the following actions: (1) notify the user of the grade, (2) make real-time adjustments to the user's training zones based upon the grade they are traversing, (3) estimate power output based upon measured grade, as well as speed and acceleration along the incline, (4) suggest a more appropriate gear ratio, and (5) actuate a gear change to the bicycle.

Natural Running Form Analysis

Two or more sensor pods 102 may be arranged on the head and body of a user. Each sensor pod 102 determines its orientation by examining the direction of gravitational acceleration when the person is standing upright. One or more of the sensor pods 102 then determines change in determined direction of gravitational acceleration as the user begins running, and may thereby determine one or more of: (1) posture—straight up or leaning forward or backwards, (2) head position—forward or neutral—and may thereby determine impact trauma, (3) knee bend angle, (4) foot strike style, and (5) inside or outside foot landing—medial or lateral.

Dynamic Bicycle Fitting

Two or more sensor pods 102 are arranged along the limbs and at joints of a user. Each sensor pod 102 determines its orientation by examining the direction of gravitational acceleration when the person is still. One or more of the sensor pods 102 then determines change in determined direction of gravitational acceleration and motion as the user begins pedaling the bicycle, and may thereby determine one or more of: (1) maximum and minimum knee angles, (2) maximum and minimum hip angles, (3) lateral knee tracking, (4) lateral hip travel, (5) maximum and minimum ankle angles, and (6) lateral ankle travel.

Cross-Country or Nordic Skiing Form Analysis

Two or more sensor pods 102 are arranged along the limbs, at joints, and on the equipment of a user. Each sensor pod 102 determines its orientation by examining the direction of gravitational acceleration when the person is still. One or more of the sensor pods 102 then determines change in determined direction of gravitational acceleration and motion as the user begins to ski, and may thereby determine one or more of: (1) maximum and minimum knee angles, (2) maximum and minimum hip angles, (3) medial and lateral knee tracking, (4) medial and lateral hip travel, (5) maximum and minimum ankle angle, (6) medial and lateral ankle travel, .and (7) ski stride power efficiency.

Notification Logging

In an embodiment, memory 106 is, at least in part, non-volatile and used for storing some or all sensor data and/or notifications (e.g., internal notification events and/or incoming notification events) for later retrieval by another device.

Heart Rate Alarm (Too High/Too Low)

In an embodiment, sensor pod 102 is configured as a personal notification alarm that notifies the user when their heart rate goes above or below specified thresholds.

Proximity Detection (Alarm when Separated)

In an embodiment, sensor pod 102 is configured as a personal notification alarm that notifies the user when one of their belongings has been removed from their immediate proximity. In this embodiment, sensor pod 102 is located with the one personal belonging and maintains wireless communication with mobile device 150, wherein mobile device 150 may raise an alarm when the wireless communication is lost.

Tweet/FB/Phone Call/Email Notification

In an embodiment, sensor pod 102 is configured as a personal notification alarm that notifies the user, using a discreet, customizable notification of one or more events, such as for example receiving a Tweet, receiving a Facebook update, receiving phone call, receiving an email, receiving a text message, and so on. Optionally, sensor pod 102 may be configured with a filter whereby notification only occurs when the event is associated with one of an identified group of people or meets some other predefined criteria.

Industrial Design Components

Compact, Low Profile Body

Sensor pod 102 is designed to fit within a compact, low-profile enclosure body that is shaped and sized similarly to one or more of a clothes button, a coin, and an Othello or checkers game piece. This small size and shape allows sensor pod 102 to be worn in several different places on the body including the wrist, chest, hip, leg, arm, stomach, head, face, and neck.

Waterproof Charging & Configuration Points & Keyed Indentations

The enclosure surface may include one or more magnets, metal post, keyed indentations and electrical contacts for charging and/or configuration without compromising water tightness. The same magnets and keyed indentations may mate with the inner body of the attachment point(s) to prevent the pod from moving relative to the attachment point. Wireless induction charging may also be used.

Attachment Point Mechanics to the Pod

Figure 2:
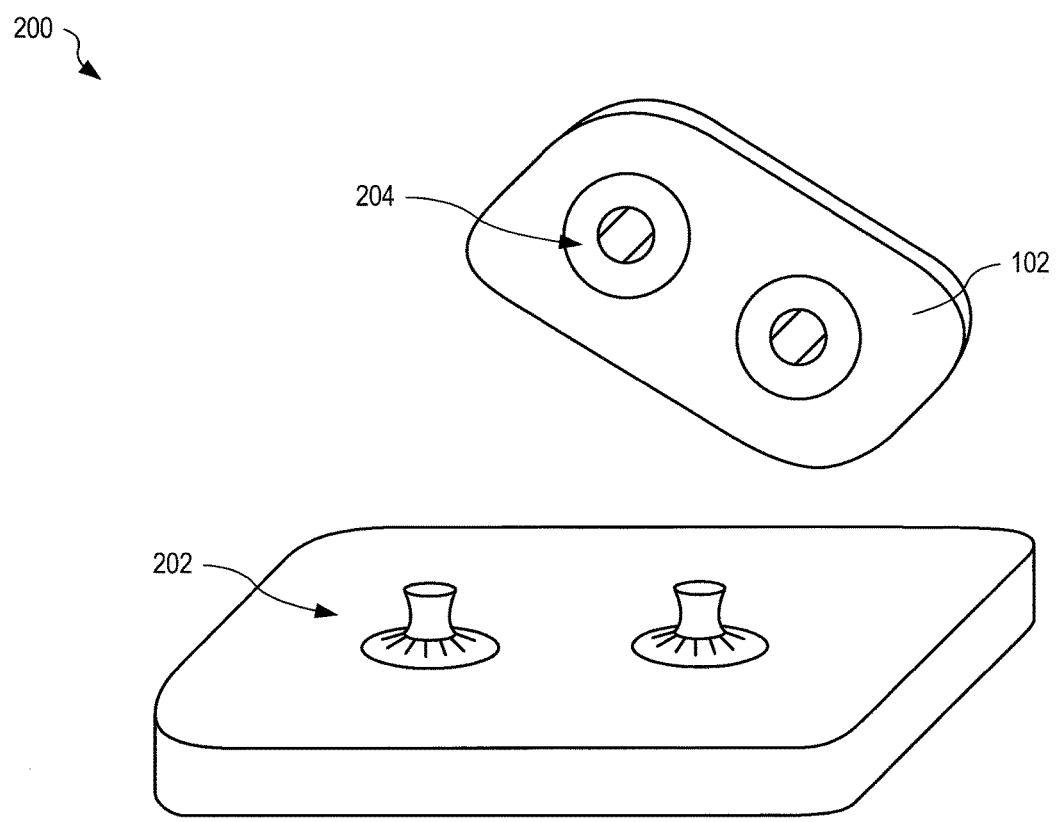
FIG. 2 shows one exemplary configuration of the sensor pod of FIG. 1 wherein the sensor pod is snap-on with a knobby post and a cavity mechanism, in an embodiment.

FIG. 2 shows one exemplary configuration of sensor pod 102 wherein pod 102 is snap-on with a knobby post 202 and a cavity 204 mechanism. Knobby post 202 and a cavity 204 are similar to snaps used to close a jacket. This concept may use watch bands, arm bands, ankle bands, waist bands, bra straps, and so on, where each of the bands or straps has two posts onto which pod 102, with the indented receptacles, connects.

Figure 3A:
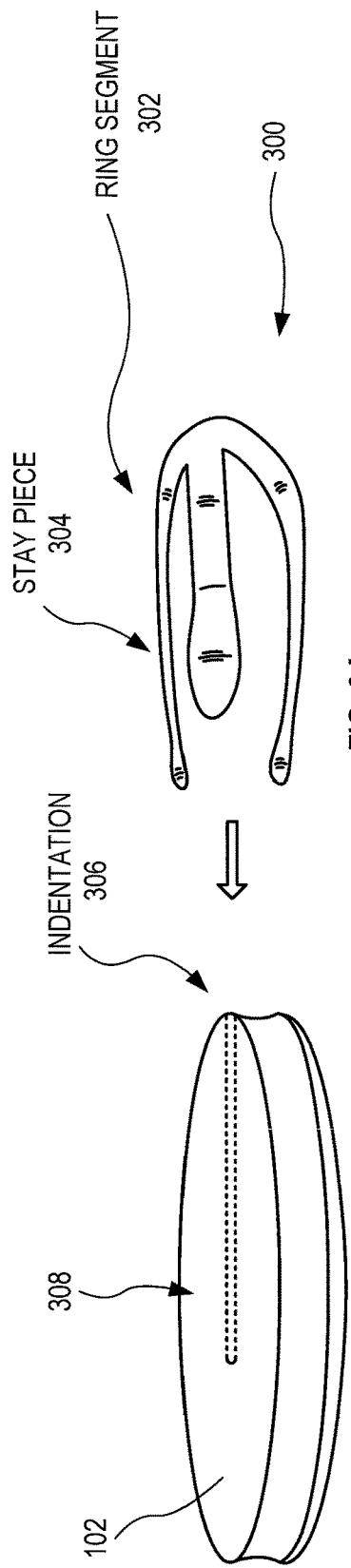
FIGS. 3A and 3B show exemplary coupling of the sensor pod of FIG. 1 with a clip formed with a ring segment and stay piece.
Figure 3B:
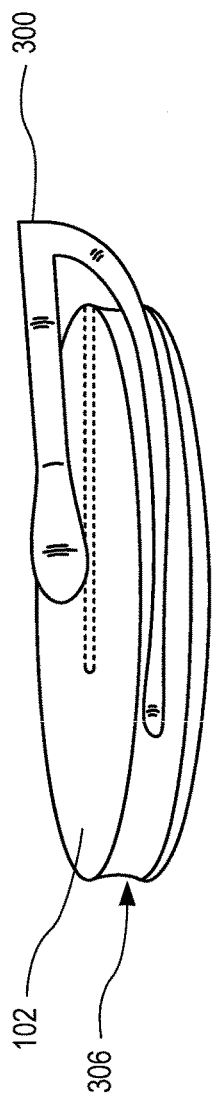

FIGS. 3A and 3B show exemplary coupling of sensor 102 with a clip 300 formed with a ring segment 302 and stay piece 304. Ring segment 302 is shaped and sized to partially encircle a groove 306 (e.g., an indentation) formed around sensor pod 102, whereupon clip 300 retains sensor pod 102. Clip 300 may behave similar to a mechanical retaining ring. Once pod 102 is retained by clip 300, clip 300 (and pod 102) may be clipped onto a band (e.g. a watchband, belt, a bra-strap etc.) or a piece of clothing (e.g., waist band on pants or shorts, shoe laces, sock cuff, etc.).

Figure 4:
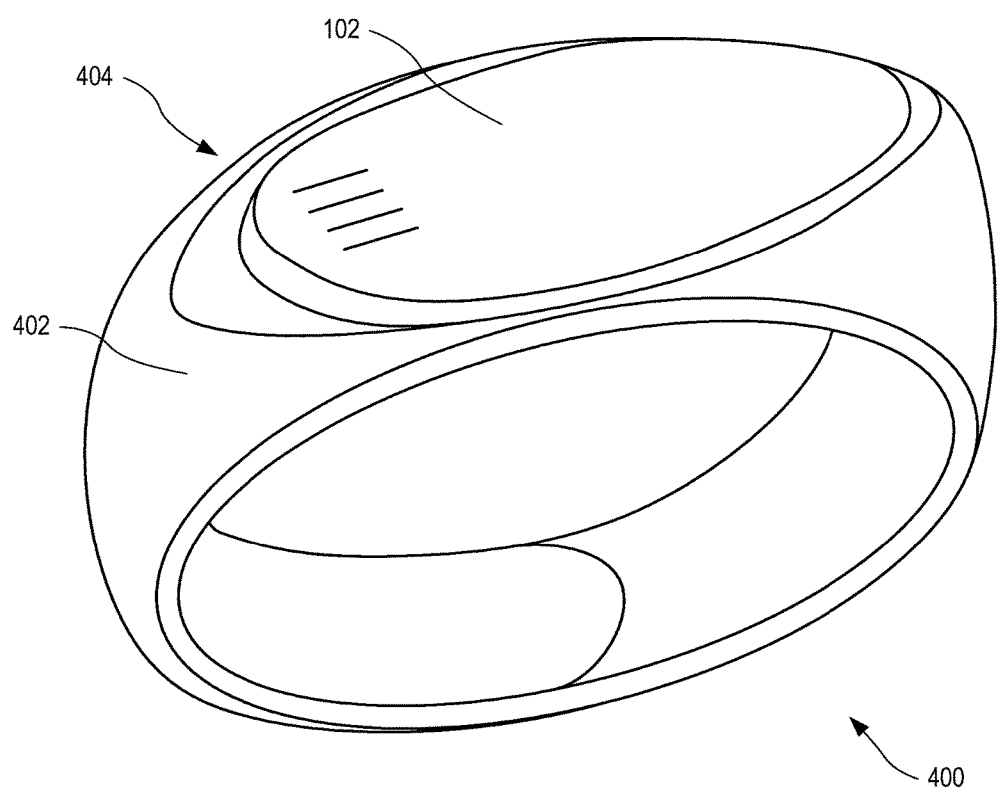
FIG. 4 shows one exemplary band formed with a pliable loop for securing to an appendage (e.g., an arm, wrist, ankle, or leg) of the user, wherein the loop is formed with an opening shaped and sized to capture the sensor pod of FIG. 1 using a groove or indentation around the pod, in an embodiment.

FIG. 4 shows one exemplary band 400 formed with a pliable loop 402 for securing to an appendage (e.g., an arm, wrist, ankle, or leg) of the user, wherein loop 402 is formed with an opening 404 shaped and sized to capture sensor pod 102 using a groove or indentation around the pod. Band 400 has a stretchable loop that may be slightly expanded to receive pod 102 such that when the stretchable loop is released, band 400 tightly grips pod 102. Band 400 may be worn on a user's wrist pod, a user's arm band, a user's anklet, and so on.

In another embodiment, a holder (e.g., clip 302 and loop 402) captures sensor pod 102 using magnetic forces.

Figure 5:
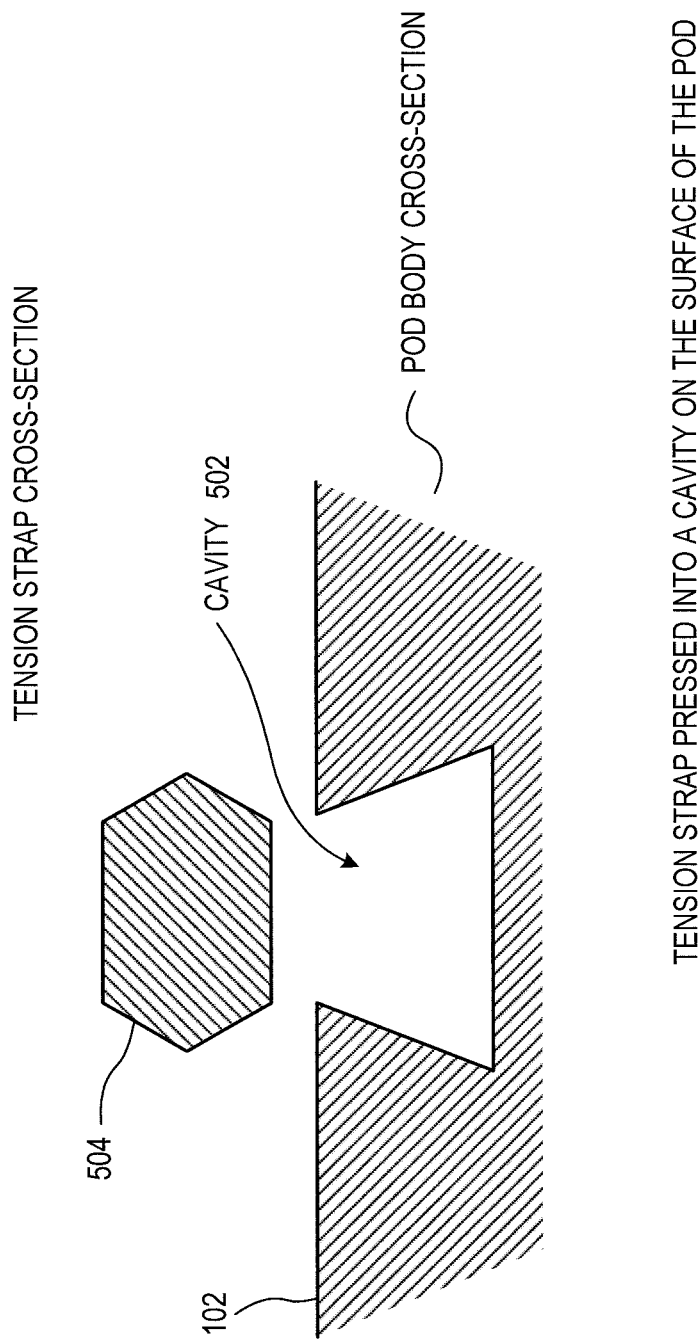
FIG. 5 shows the sensor pod of FIG. 1 formed with a cavity for removably capturing a tension strap, in an embodiment.

FIG. 5 shows sensor pod 102 formed with a cavity 502 for removably capturing a tension strap 504, which thereby secures sensor pod 102 in place. Cavity 502 operates as a press fit connector, similar to cavity 204 that couples with knobby post 202. Cavity 502 may be used to couple with a piece of clothing or may be used to couple with part of a removable band or strap.

In another embodiment, sensor pod 102 is configured within one or more holes (along any axis of sensor pod 102) into which one or more posts are inserted to removably secure sensor pod 102 in place. For example, pins or clips may be inserted into one or more of the holes in pod 102 and connected to a strap, thereby allowing pod 102 to be connected to a user's arm or leg. Alternately, the pins or clips may allow pod 102 to be worn like a pendant.

In another embodiment, sensor pod 102 is captured by a form-fitting overmold that secures sensor pod 102 in place. In another embodiment, sensor pod 102 is configured with a key hole, wherein a key chain couples therewith to secure sensor pod 102 in place. In another embodiment, sensor pod 102 is secured within a pocket (e.g., a pocket of a garment worn by a user of sensor pod 102).

Attachment Point Mechanics to Clothing/Accessories

Sensor pod 102 and/or its capturing device (e.g., clip 302, loop 402) is formed to couple with clothing and/or accessories of a user of sensor pod 102 in a number of different ways. Sensor pod 102 and/or its capturing device may be configured to couple with one or more of (a) Wrist Watch Backing, (b) Wrist Watch Band Keeper, (c) Wrist Band Enclosure, (d) Arm Band with optional smartphone/music player sleeve, (e) Ankle Band, (f) Bra Strap Clip, (g) Bra Cup Clip, (h) Bra Underwire Clip, (i) Shorts Elastic Clip, (j)

Sport Sock Clip, (k) Shirt Sleeve Clip, (l) Fabric Gripping Enclosure, (m) Jewelry, (n) Headband, (o) Helmet, (p) Hosiery, and (q) Clothing.

Some Example Attachment Point Embodiments

Sensor pod 102 may be attached to a user's body at many different points. That is, by selecting the appropriate attachment mechanism, sensor pod 102 may attach to a user at any convenient and practical position. The following provides examples of attachment devices and methods.

Form-Fitting Overmold Wrist Watch Backing

This is a somewhat stiff, hollow form-fitting overmold that fits onto the pod, and may be secured to the back of a wrist watch module. The form-fitting overmold may be adhered to the watch underside using an adhesive, or may have small, pliable loops co-molded or otherwise attached to the form-fitting overmold that may be used to secure the form-fitting overmold to the watch band.

Pliable Loop Wrist Watch Backing

This is a pliable ring co-molded or otherwise attached to two smaller, pliable loops. A girth indentation of the sensor pod 102 fits within the ring, and the co-molded loops secure the ring (and hence sensor pod 102) to a wrist band.

Form-Fitting Overmold Wrist Watch Band Keeper Attachment

This is a somewhat stiff, hollow form-fitting overmold for capturing sensor pod 102 and includes a wrist band keeper through which to feed a watch wrist band and/or a clip intended to hold compressive force against the wrist watch band.

Form-Fitting Overmold Wrist Band

This is a wrist band co-molded or otherwise attached to a hollow form-fitting overmold that fits onto sensor pod 102 and may be secured around the wrist.

Pliable Loop Wrist Band

As shown in FIG. 4, a wrist band is co-molded or otherwise attached to a pliable loop which wraps around the girth indentation of sensor pod 102.

Pocket Arm Band Enclosure with Smartphone/Music Player Sleeve

This is a fabric band with a re-closable pocket to hold sensor pod 102 against skin of a user wearing the fabric band. An opening in the inside face of the pocket provides a sightline between the PPG interface of sensor pod 102 and the skin. The band may also have a transparent, touch-through sleeve for holding a mobile device, such as one of a smart phone, a handheld media player, and other similar compute devices.

Ring Segment Bra Strap Clip

This ring segment bra strap clip has a ring segment attached to a clip configured to hold compressive force against a bra strap. The ring segment captures sensor pod 102 around a girth indentation. The clip may be covered in a soft fabrication material to prevent deterioration or damage to the bra strap fabric.

Form-Fitting Overmold Bra Cup Clip

This clip is a somewhat stiff, hollow form-fitting overmold for capturing sensor pod 102. The clip includes an attached clip configured to hold compressive force against the bra cup. The clip may be covered in a soft fabrication material to prevent deterioration or damage to the bra cup fabric.

Ring Segment Bra Underwire Clip

A ring segment bra underwire clip includes a ring segment attached to two clips configured hold compressive force against an underwire of a bra, such that sensor pod 102, when captured by the ring segment around a girth indentation of the pod, positions sensor pod 102 between two cups of the bra and against the skin of the user. The clip may be covered in a soft fabrication material to prevent deterioration or damage to the bra underwire fabric.

Form-Fitting Overmold Shorts Elastic Clip

A form-fitting overmold shorts elastic clip has a somewhat stiff, hollow form-fitting overmold for capturing sensor pod 102 and an attached clip configured to hold compressive force against a waist elastic band of a pair of shorts. The clip may be covered in a soft fabrication material to prevent deterioration or damage to the waist elastic fabric.

Ring Segment Sport Sock Clip

A ring segment sports sock clip has a ring segment for capturing sensor pod 102 around an indented girth and is attached to two clips configured to hold compressive force against the sport sock elastic. The clip may be covered in a soft fabrication material to prevent deterioration or damage to the sport sock elastic fabric.

Form-Fitting Overmold Shirt Sleeve Clip

A form-fitting overmold shirt sleeve clip has a somewhat stiff, hollow form-fitting overmold for capturing sensor pod 102 and an attached clip configured to hold compressive force against the arm sleeve elastic of a shirt. The clip may be covered in a soft fabrication material to prevent deterioration or damage to the arm sleeve elastic fabric.

Fabric Gripping Form-Fitting Overmold

A fabric gripping form-fitting overmold has a somewhat stiff, hollow form-fitting overmold configured with a roughness and/or protrusions on the top to anchor the overmold into a tightly fitting fabric (e.g, spandex/lycra clothing) to prevent lateral movement of the overmold and captured sensor pod 102.

Figure 6A:
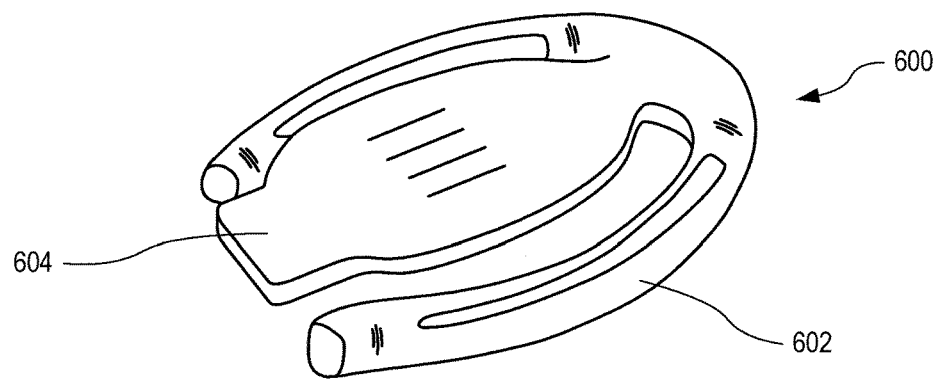
FIGS. 6A, 6B, and 6C show one exemplary belt clip, molded in rigid plastic, for capturing the sensor pod of FIG. 1, in an embodiment.
Figure 6B:
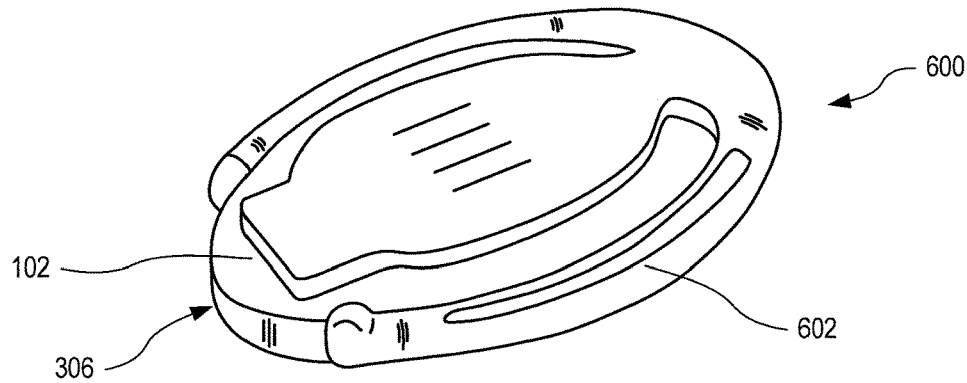
Figure 6C:
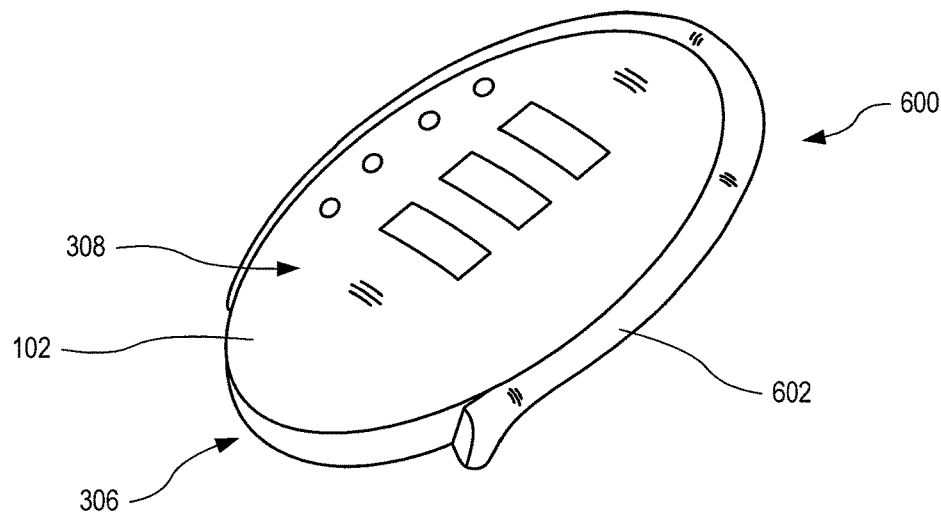

FIGS. 6A, 6B, and 6C show one exemplary belt clip 600 that is molded in a rigid plastic. Belt clip 600 has a ring segment 602 that is shaped and sized to capture sensor pod 102 around a girth indentation 306, and a belt segment 604 that is configured to apply pressure to a belt. An active surface 308 of sensor pod 102 is thereby held against skin of a user.

Integrated Clothing, Body-Worn Accessories, Protective Equipment

In an embodiment, integration of sensor pod 102 into an article and/or apparel may be facilitated by a pocket sewn into or otherwise fabricated with the article and/or apparel. The pocket is formed to hold sensor pod 102 in a desired position such that active surface 308 of sensor pod 102 is in close proximity to skin of the user (e.g., wearer of the article and/or apparel). The article and/or apparel could be one or more of clothing, jewelry, armbands, headbands, helmets, garter, hosiery, and similarly worn items.

Sport Bra with Pocket

In this embodiment, a women's sport bra is fabricated with one or more re-closable pockets that each may hold sensor pod 102. An opening in the inside face of the pocket allows active surface 308 of sensor pod 102 access to the user's skin (e.g., a sightline between a PPG interface of sensor pod 102 and the user's skin).

Control Top Bra with Pocket

In this embodiment, a women's control top bra is configured with one or more re-closable pockets that each may hold sensor pod 102. An opening in the inside face of the pocket allows active surface 308 of sensor pod 102 access to the user's skin (e.g., a sightline between a PPG interface of sensor pod 102 and the user's skin).

Exercise Top with Pocket

In this embodiment, an exercise top is fabricated with one or more re-closable pockets that each may hold sensor pod 102. An opening in the inside face of the pocket allows active surface 308 of sensor pod 102 access to the user's skin (e.g., a sightline between a PPG interface of sensor pod 102 and the user's skin).

Wetsuit with Pocket

In this embodiment, a wetsuit is configured with one or more re-closable pockets that each may hold sensor pod 102. An opening in the inside face of the pocket allows active surface 308 of sensor pod 102 access to the user's skin (e.g., a sightline between a PPG interface of sensor pod 102 and the user's skin).

Cycling Jersey with Pocket

In this embodiment, a cycling jersey is configured with one or more re-closable pockets that each may hold sensor pod 102. An opening in the inside face of the pocket allows active surface 308 of sensor pod 102 access to the user's skin (e.g., a sightline between a PPG interface of sensor pod 102 and the user's skin).

Cycling Shorts with Pocket

In this embodiment, a pair of cycling shorts is configured with one or more re-closable pockets that each may hold sensor pod 102. An opening in the inside face of the pocket allows active surface 308 of sensor pod 102 access to the user's skin (e.g., a sightline between a PPG interface of sensor pod 102 and the user's skin).

Gloves with Pocket

In this embodiment, a pair of gloves is configured with one or more re-closable pockets that each may hold sensor pod 102. An opening in the inside face of the pocket allows active surface 308 of sensor pod 102 access to the user's skin (e.g., a sightline between a PPG interface of sensor pod 102 and the user's skin).

Shorts with Pocket

In this embodiment, a pair of brief underpants is configured with one or more re-closable pockets that each may hold sensor pod 102. An opening in the inside face of the pocket allows active surface 308 of sensor pod 102 access to the user's skin (e.g., a sightline between a PPG interface of sensor pod 102 and the user's skin).

Helmet with Pliable Loop and Strap

In this embodiment, a helmet is configured with attachment mechanics to hold active surface 308 of sensor pod 102 against skin of the user's head.

Elbow Pad with Pocket

In this embodiment, an elbow pad is configured with one or more re-closable pockets or other attachment mechanics that each may hold sensor pod 102. An opening in the inside face of the pocket allows active surface 308 of sensor pod 102 access to the user's skin (e.g., a sightline between a PPG interface of sensor pod 102 and the user's skin).

Knee Pad with Pocket

In this embodiment, a knee pad is configured with one or more re-closable pockets or other attachment mechanics that each may hold sensor pod 102. For example, an opening in the inside face of the pocket allows active surface 308 of sensor pod 102 access to the user's skin (e.g., a sightline between a PPG interface of sensor pod 102 and the user's skin).

Wrist Guard with Pocket

In this embodiment, a wrist guard is configured with one or more re-closable pockets or other attachment mechanics that each may hold sensor pod 102. An opening in the inside face of the pocket allows active surface 308 of sensor pod 102 access to the user's skin (e.g., a sightline between a PPG interface of sensor pod 102 and the user's skin).

Shin Pad with Pocket

In this embodiment, a shin pad is configured with one or more re-closable pockets or other attachment mechanics that each may hold sensor pod 102. An opening in the inside face of the pocket allows active surface 308 of sensor pod 102 access to the user's skin (e.g., a sightline between a PPG interface of sensor pod 102 and the user's skin).

Swim Cap with Pocket

In this embodiment, a swim cap is configured with one or more re-closable pockets that each may hold sensor pod 102. An opening in the inside face of the pocket allows active surface 308 of sensor pod 102 access to the user's skin (e.g., a sightline between a PPG interface of sensor pod 102 and the user's skin).

Headband with Pocket

In this embodiment, a headband is configured with one or more re-closable pockets or other attachment mechanics that each may hold sensor pod 102. An opening in the inside face of the pocket allows active surface 308 of sensor pod 102 access to the user's skin (e.g., a sightline between a PPG interface of sensor pod 102 and the user's skin).

Neckband with Pocket

In this embodiment, a neckband is configured with one or more re-closable pockets or other attachment mechanics that each may hold sensor pod 102. An opening in the inside face of the pocket allows active surface 308 of sensor pod 102 access to the user's skin (e.g., a sightline between a PPG interface of sensor pod 102 and the user's skin).

Neck Warmer with Pocket

In this embodiment, a neck warmer is configured with one or more re-closable pockets or other attachment mechanics that each may hold sensor pod 102. An opening in the inside face of the pocket allows active surface 308 of sensor pod 102 access to the user's skin (e.g., a sightline between a PPG interface of sensor pod 102 and the user's skin).

Wool Cap/Toque with Pocket

In this embodiment, a wool cap (toque) is configured with one or more re-closable pockets or other attachment mechanics that each may hold sensor pod 102. An opening in the inside face of the pocket allows active surface 308 of sensor pod 102 access to the user's skin (e.g., a sightline between a PPG interface of sensor pod 102 and the user's skin).

Baseball Cap with Pocket

In this embodiment, a baseball cap is configured with one or more re-closable pockets or other attachment mechanics that each may hold sensor pod 102. An opening in the inside face of the pocket allows active surface 308 of sensor pod 102 access to the user's skin (e.g., a sightline between a PPG interface of sensor pod 102 and the user's skin).

Jockey Helmet with Pocket

In this embodiment, a jockey helmet is configured with one or more re-closable pockets or other attachment mechanics that each may hold sensor pod 102. An opening in the inside face of the pocket allows active surface 308 of sensor pod 102 access to the user's skin (e.g., a sightline between a PPG interface of sensor pod 102 and the user's skin).

Combination of Features

Features described above as well as those claimed below may be combined in various ways without departing from the scope hereof. The following examples illustrate possible, non-limiting combinations the present invention has been described above, it should be clear that many changes and modifications may be made to the process and product without departing from the spirit and scope of this invention:

(A) A system for biometric sensing with sensor fusion, includes a first sensor for coupling with a user and being capable of sensing a first characteristic of the user, a second sensor for coupling with the user and being capable of sensing a second characteristic of the user, a processor, and a memory storing software having machine readable instructions that when executed by the processor implement an algorithm to correct for motion artifacts included within the second characteristic based upon activity of the user determined from the first characteristic.

(B) In the system denoted as (A), further including a first pod for containing the first and second sensors, the processor, and the memory.

(C) In either of the systems denoted as (A) and (B), further including a first pod for positioning on a first part of the user's body and containing the first sensor, a second pod for positioning on a second part of the user's body different from the first part, and containing the processor, the memory, and the second sensor, a first transceiver configured with the first pod for transmitting the first characteristic, and a second transceiver configured with the second pod for receiving the first characteristic.

(D) In any of the systems denoted as (A) through (C), further including an output device configured within the first pod for outputting a signal to the user in response to a command received from the second pod.

(E) In the system denoted as (D), the output device comprising a haptic device.

(F) In any of the systems denoted as (C) through (E), the second pod comprising a smart phone.

(G) In any of the systems denoted as (C) through (F), the software further including sensor network management capable of automatically identifying the first and the second pods and determining the algorithm for correcting motion artifacts.

(H) In any of the systems denoted as (C) through (G), the software further including sensor network management capable of automatically identifying location of the first and second pods on the user's body.

(I) In any of the systems denoted as (A) through (H), the software further comprising a calibration algorithm for calibrating the first characteristic based upon the second characteristic.

(J) In any of the systems denoted as (A) through (I), the first and second characteristics being selected from the group including: heart rate, respiration, motion, skin temperature, galvanic skin response, and $O_2$ saturation.

(K) In any of the systems denoted as (A) through (J), the first and second sensor selected from the group including: pressure sensor, ultrasonic sensor, laser sensor, PPG sensor, RF sensor, ECG sensor, motion sensor, respiration sensor, temperature sensor, and galvanic skin response sensor.

(L) A method for biometric sensing with sensor fusion, includes determining, within a first pod positioned at a first location of a user's body, a first characteristic of the user, receiving, within the first pod, a wireless signal indicative of a second characteristic of the user from a second pod positioned at a second location of the user's body, and determining an activity of the user based upon the first and second characteristics.

(M) In the method denoted as (L), further including correcting for motion artifacts within the first characteristic based upon the second characteristic.

(N) In either of the methods denoted as (L) and (M), the step of correcting including determining a motion of the user based upon the first characteristic and the first location, and subtracting, prior to the step of determining the activity, the motion from the first characteristic.

(O) In any of the method denoted as (L) through (N), further including calibrating the activity based upon the first characteristic.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A system for biometric sensing using sensor fusion, comprising:
    a first pod configured to be positioned on a first body part of a user, the first pod including:
        a first sensor configured to couple with the first body part to sense movement characteristics of the user; and
        a first transceiver configured to transmit the movement characteristics; and
    a second pod configured to be positioned on a second body part of the user different from the first body part, the second pod including:
        a second sensor configured to couple with the second body part to sense biometric characteristics of the user;
        a second transceiver configured to receive the movement characteristics from the first pod;
        a processor; and
        a memory storing machine-readable instructions that, when executed by the processor, control the processor to implement an algorithm to correct for motion artifacts within the biometric characteristics based upon an activity of the user determined from the movement characteristics.

2. The system of claim 1, the first pod including an output device configured to output a signal to the user in response to a command received from the second pod.

3. The system of claim 2, the output device comprising a haptic device.

4. The system of claim 1, the second pod comprising a smart phone.

5. The system of claim 1, the memory storing additional machine-readable instructions that control the processor to:
    automatically identify the first pod and the second pod, and
    determine the algorithm to correct for the motion artifacts.

6. The system of claim 1, the memory storing additional machine-readable instructions that control the processor to identify a location of the first pod on the user and a location of the second pod on the user.

* * * * *